United States Patent
Jimenez et al.

(10) Patent No.: US 12,303,017 B2
(45) Date of Patent: *May 20, 2025

(54) ORAL CARE IMPLEMENT

(71) Applicant: Colgate-Palmolive Company, New York, NY (US)

(72) Inventors: Eduardo Jimenez, Manalapan, NJ (US); Douglas Hohlbein, Hopewell, NJ (US); Patrik Johansson, Hoboken, NJ (US)

(73) Assignee: Colgate-Palmolive Company, New York, NY (US)

( * ) Notice: Subject to any disclaimer, the term of this patent is extended or adjusted under 35 U.S.C. 154(b) by 67 days.

This patent is subject to a terminal disclaimer.

(21) Appl. No.: 17/844,197

(22) Filed: Jun. 20, 2022

(65) Prior Publication Data

US 2022/0312949 A1    Oct. 6, 2022

Related U.S. Application Data

(63) Continuation of application No. 16/343,146, filed as application No. PCT/US2016/057613 on Oct. 19, 2016, now Pat. No. 11,382,413.

(51) Int. Cl.
*A46B 17/06* (2006.01)
*A61L 2/10* (2006.01)
*A46B 11/00* (2006.01)

(52) U.S. Cl.
CPC .............. *A46B 17/065* (2013.01); *A61L 2/10* (2013.01); *A46B 11/00* (2013.01)

(58) Field of Classification Search
CPC ....... A46B 17/065; A46B 11/00; A46B 17/04; A46B 15/0095; A46B 2200/1066; A46B 15/0034; A61L 2/10

See application file for complete search history.

(56) References Cited

U.S. PATENT DOCUMENTS 3,277,358 A    10/1966  Nicholl
3,667,454 A *  6/1972  Prince ............... A61C 17/3481
                                                  15/159.1

(Continued)

FOREIGN PATENT DOCUMENTS

CN    101731984    6/2010
CN    102665482    9/2012

(Continued)

OTHER PUBLICATIONS

Illustration of Electrical Knowledge, Science Education Research Association, Hunan Science & Technology Press, published Apr. 2016, p. 101.

(Continued)

*Primary Examiner* — Regina M Yoo

(57) ABSTRACT

An oral care implement sanitization system that includes an oral care implement and a case for storing the oral care implement and activating a sanitization or sterilization procedure. The oral care implement may include tooth cleaning elements, a light source, and a first electrical coupling element operably coupled to the light source. The case may include a housing having a cavity for holding the oral care implement, a power source, and a second electrical coupling element operably coupled to the power source. When the oral care implement is positioned within the cavity of the housing of the case, the first and second electrical coupling elements are operably coupled together. Operable coupling of the first and second electrical coupling elements initiates, either immediately or upon the occurrence of some additional action, activation of the light source for sanitizing or sterilizing the tooth cleaning elements.

15 Claims, 15 Drawing Sheets

(56) References Cited

U.S. PATENT DOCUMENTS

| | | | | |
|---|---|---|---|---|
| 3,954,407 A | * | 5/1976 | Andary | A61L 2/10 250/455.11 |
| 4,411,041 A | | 10/1983 | Braga | |
| 4,772,214 A | | 9/1988 | Stoegmueller | |
| 4,806,770 A | * | 2/1989 | Hylton | A47K 1/09 250/455.11 |
| 4,906,851 A | * | 3/1990 | Beasley | A61L 2/10 250/455.11 |
| 5,003,250 A | * | 3/1991 | Hukuba | G01R 19/155 320/132 |
| 5,127,521 A | * | 7/1992 | Bourque | A61L 2/10 206/362.1 |
| 6,096,264 A | * | 8/2000 | Peifer | H02J 7/0044 D6/528 |
| 6,171,559 B1 | * | 1/2001 | Sanders | A61L 2/18 134/144 |
| 6,752,627 B2 | | 6/2004 | Lin | |
| 6,753,537 B2 | | 6/2004 | Woo | |
| 8,168,963 B2 | | 5/2012 | Ratcliffe | |
| 8,695,146 B2 | | 4/2014 | Waguespack et al. | |
| 8,707,504 B2 | | 4/2014 | Ryan | |
| 8,809,807 B2 | * | 8/2014 | Nelson | A61L 2/10 250/455.11 |
| 9,000,398 B2 | | 4/2015 | Nelson et al. | |
| 9,186,229 B2 | | 11/2015 | Vu et al. | |
| 9,337,675 B2 | | 5/2016 | Jung et al. | |
| 9,457,199 B2 | | 10/2016 | Lin | |
| 9,510,665 B2 | | 12/2016 | Lombardi | |
| 9,717,325 B2 | | 8/2017 | Mongan et al. | |
| 9,756,932 B2 | | 9/2017 | Mongan et al. | |
| 10,058,169 B2 | | 8/2018 | Gorelick | |
| 10,426,251 B2 | | 10/2019 | Sprosta et al. | |
| 10,674,810 B2 | | 6/2020 | Bloch | |
| 2004/0099812 A1 | * | 5/2004 | Humphreys | A61L 2/04 250/455.11 |
| 2004/0155201 A1 | | 8/2004 | Russell et al. | |
| 2006/0213792 A1 | * | 9/2006 | Nguyen | E03D 9/00 206/349 |
| 2007/0131241 A1 | | 6/2007 | Nanda | |
| 2007/0295916 A1 | | 12/2007 | Reuben | |
| 2008/0060153 A1 | | 3/2008 | Jansheski | |
| 2008/0060829 A1 | | 3/2008 | Jansheski | |
| 2008/0131834 A1 | * | 6/2008 | Shepherd | A46B 15/0034 433/29 |
| 2008/0209650 A1 | | 9/2008 | Brewer et al. | |
| 2008/0219883 A1 | * | 9/2008 | Thur | A61L 2/04 422/307 |
| 2008/0265179 A1 | * | 10/2008 | Havens | A61L 2/10 250/492.1 |
| 2009/0083924 A1 | * | 4/2009 | Shepherd | A46B 15/0002 15/105 |
| 2009/0256085 A1 | * | 10/2009 | Thiruppathi | A61L 2/10 250/492.1 |
| 2010/0044582 A1 | * | 2/2010 | Cooper | A61L 2/10 250/455.11 |
| 2011/0024647 A1 | | 2/2011 | Hsu | |
| 2011/0100865 A1 | | 5/2011 | Brink | |
| 2011/0126370 A1 | | 6/2011 | Reuben | |
| 2011/0162155 A1 | | 7/2011 | Wai | |
| 2011/0296643 A1 | * | 12/2011 | Shepherd | A61N 5/0603 15/167.1 |
| 2011/0309268 A1 | | 12/2011 | Parker | |
| 2011/0315572 A1 | * | 12/2011 | Vu | A61C 19/02 206/216 |
| 2012/0318689 A1 | * | 12/2012 | Joseph | B65D 51/248 206/234 |
| 2014/0135798 A1 | | 5/2014 | David | |
| 2014/0217131 A1 | | 8/2014 | Wang et al. | |
| 2014/0259474 A1 | * | 9/2014 | Sokol | A61C 17/02 15/22.2 |
| 2016/0073830 A1 | * | 3/2016 | McClenon | A47K 1/09 34/202 |
| 2016/0317268 A1 | | 11/2016 | Dietzel et al. | |
| 2017/0360973 A1 | | 12/2017 | Saue | |
| 2019/0313785 A1 | | 10/2019 | Jimenez et al. | |

FOREIGN PATENT DOCUMENTS

| | | | | |
|---|---|---|---|---|
| CN | 102665483 | | 9/2012 | |
| CN | 103876457 | | 6/2014 | |
| GB | 1195209 A | * | 6/1970 | A61C 1/0015 |
| KR | 20110000232 | | 1/2011 | |
| KR | 20110054985 A | * | 5/2011 | A61L 2/10 |
| KR | 20140048790 A | * | 4/2014 | A61L 2/10 |
| WO | 2016/143974 | | 9/2016 | |
| WO | 2018/075021 | | 4/2018 | |

OTHER PUBLICATIONS

International Search Report and Written Opinion of the International Searching Authority in International Application No. PCT/US2016/057613, mailed Sep. 25, 2017.

Jiang Minhua, Amazing New Materials, Shandong Science & Technology Press, published Oct. 2013, pp. 211-212.

Mei Yi, Encyclopedia of Household Appliances in China, Encyclopedia of China Publishing House, published Mar. 1991, p. 79.

You, translator, Illustration of Electrical Knowledge, Science Education Research Association, Hunan Science & Technology Press, published Apr. 2016, p. 101.

* cited by examiner

ORAL CARE IMPLEMENT

CROSS-REFERENCE TO RELATED APPLICATIONS

The present application is a continuation of U.S. patent application Ser. No. 16/343,146, filed Apr. 18, 2019, which is a national stage entry of PCT/US2016/057613, filed Oct. 19, 2016, the entireties of which are incorporated herein by reference.

BACKGROUND

Regular sanitization of an oral care implement such as a toothbrush is desirable to kill harmful germs and bacteria often found on the cleaning elements or bristles of the oral care implement. It has previously been known to apply ultraviolet light to the oral care implement to kill these harmful germs and bacteria. However, prior attempts to use ultraviolet light to kill germs and bacteria on oral care implements are deficient for several reasons. Specifically, previous systems that use ultraviolet light to sanitize oral care implements may expose the user of the oral care implement to the ultraviolet light, which can be harmful to the user. Additionally, such prior systems fail to focus the ultraviolet light on the base of the tooth cleaning elements which is the region that is most likely to harbor bacteria growth. Finally, such prior systems are costly particularly where the circuitry is formed as a part of the oral care implement which must be replaced fairly frequently. An oral care implement sanitization system that overcomes the above-noted deficiencies in a cost-effective and ready-to-use manner is needed.

BRIEF SUMMARY

The present invention may be directed, in one aspect, to an oral care implement sanitization system that includes an oral care implement and a case for storing the oral care implement and activating a sanitization or sterilization procedure. The oral care implement may include tooth cleaning elements, a light source, and a first electrical coupling element operably coupled to the light source. The case may include a housing having a cavity for holding the oral care implement, a power source, and a second electrical coupling operably coupled to the power source. When the oral care implement is positioned within the cavity of the housing of the case, the first and second electrical coupling elements are operably coupled together. The first and second electrical coupling elements may be pairs of electrical contacts, inductive coils, or the like. Operable coupling of the first and second electrical coupling elements initiates, either immediately or upon the occurrence of some additional action, activation of the light source for sanitizing or sterilizing the tooth cleaning elements.

In one aspect, the invention may be an oral care implement sanitization system comprising: an oral care implement comprising: a body having a handle portion and a head portion, a plurality of tooth cleaning elements extending from the head portion; a light source located in the head portion and configured to sanitize the plurality of tooth cleaning elements; and a first electrical coupling element operably coupled to the light source; a case for storing the oral care implement and activating the light source to sanitize the plurality of tooth cleaning elements, the case comprising: a housing comprising a cavity for holding the oral care implement; a power source; and a second electrical coupling element operably coupled to the power source; and wherein when the oral care implement is positioned within the cavity of the housing of the case, the first electrical coupling element of the oral care implement is operably coupled to the second electrical coupling element of the case.

In another aspect, the invention may be a kit for storage and sanitization of a toothbrush, the kit comprising: a toothbrush comprising: a body having a plurality of tooth cleaning elements extending therefrom; a light source configured to sanitize the plurality of tooth cleaning elements; and a first electrical coupling element operably coupled to the light source; a case comprising: a housing having a cavity for holding the toothbrush; a power source; and a second electrical coupling element operably coupled to the power source; and wherein when the toothbrush is positioned within the cavity of the housing of the case, the first electrical coupling element is operably coupled to the second electrical coupling element and the light source is activated to transmit UV light towards the plurality of tooth cleaning elements.

In yet another aspect, the invention may be an oral care implement sanitization system comprising: an oral care implement comprising: a handle and a head that is detachably coupled to the handle, a plurality of tooth cleaning elements extending from the head; a light source configured to sanitize the plurality of tooth cleaning elements; and a first electrical coupling element operably coupled to the light source; a case for storing the oral care implement and activating the light source to sanitize the plurality of tooth cleaning elements, the case comprising: a housing comprising a cavity for holding the oral care implement; a power source; and a second electrical coupling element operably coupled to the power source; and wherein when the oral care implement is positioned within the cavity of the housing of the case, the first electrical coupling element of the oral care implement is operably coupled to the second electrical coupling element of the case and the light source is activated for a predetermined period of time.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
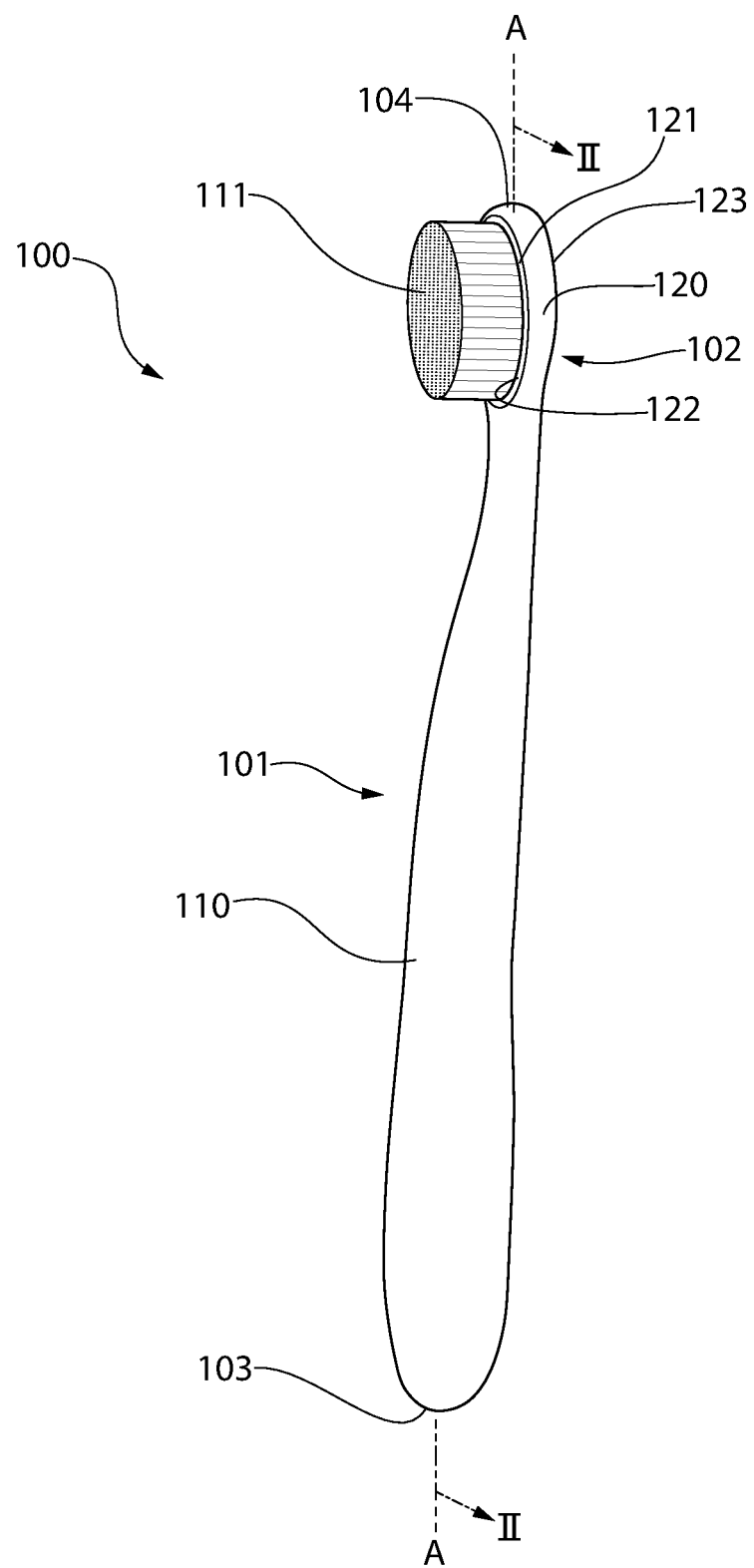
FIG. 1 is front perspective view of an oral care implement in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Referring to FIG. 1, an oral care implement 100 is illustrated in accordance with an embodiment of the present invention. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having cleaning elements, or any other type of implement that is commonly used for oral care. In embodiments that user a powered toothbrush, the toothbrush could have bristles that are vibrated by a motor and eccentric or bristles that are on a plate that rotates/oscillates. In some embodiments the oral care implement 100 may be any type of personal care implement, and not one that is specifically used for oral care, such as a deodorant application implement, a face or body cleaning implement, a razor, a hairbrush, or the like. Basically, the invention is directed to a system for sanitizing the oral care implement 100, and thus any type of implement which might require sanitization, whether it be for oral care, personal care, or other type of care, can be used as the oral care implement in various embodiments.

The oral care implement 100 comprises a body 101 having a handle portion 110 and a head portion 120. The oral care implement 100 extends from a proximal end 103 to a distal end 104 along a longitudinal axis A-A. In the exemplified embodiment the body 101, including the handle portion 110 and the head portion 120, is an integral structure that is formed as a single, unitary component. Furthermore, the oral care implement 100 in the exemplified embodiment includes a head plate 121 that is coupled to the head portion 120 of the body 101 to form a head 102 of the oral care implement 100. Thus, the head 102 comprises both the head portion 120 and the head plate 121 in the exemplified embodiment. In other embodiments, the head plate 121 may be omitted to form a more conventional style oral care implement that uses staple technology for securing the tooth cleaning elements to the head.

The handle portion 110 is an elongated structure that provides the mechanism by which the user can hold and manipulate the oral care implement 100 during use. In the exemplified embodiment, the handle portion 110 is generically depicted having various contours for user comfort. Of course, the invention is not to be limited by the specific shape illustrated for the handle portion 110 in all embodiments and in certain other embodiments the handle portion 110 can take on a wide variety of shapes, contours, and configurations, none of which are limiting of the present invention unless so specified in the claims.

The handle portion 110 may be formed of a hard or rigid plastic material, such as for example without limitation polymers and copolymers of ethylene, propylene, butadiene, vinyl compounds, and polyesters such as polyethylene terephthalate. The handle portion 110 may also include a grip that is formed of a resilient/elastomeric material, such as a thermoplastic elastomer. Such a grip may be molded over a portion of the handle portion 110 that is typically gripped by a user's thumb and forefinger during use. Furthermore, it should be appreciated that additional regions of the handle portion 110 can be overmolded with the resilient/elastomeric material to enhance the gripability of the handle portion 110 during use. For example, portions of the handle portion 110 that are typically gripped by a user's palm during use may be overmolded with a thermoplastic elastomer or other resilient material to further increase comfort to a user. Furthermore, materials other than those noted above can be used to form the handle portion 110, including metal, wood, or any other desired material that has sufficient structural rigidity to permit a user to grip the handle portion 110 and manipulate the oral care implement 100 during oral care activities such as toothbrushing or personal care activities such as facial cleansing.

The head portion 120 of the oral care implement 100 is coupled to the handle portion 110 and comprises a front surface 122 and an opposing rear surface 123. In the exemplified embodiment, the head portion 120 is formed integrally with the handle portion 110 as a single unitary structure using a molding (i.e., injection molding), milling, machining, or other suitable process. However, in other embodiments the handle portion 110 and the head portion 120 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Thus, the head portion 120 may, in certain embodiments, be formed of any of the rigid plastic materials described above as being used for forming the handle portion 110, although the invention is not to be so limited in all embodiments and other materials that are commonly used during toothbrush head manufacture may also be used.

In the exemplified embodiment, a plurality of tooth cleaning elements 111 are coupled to and extend from the head portion 120 of the oral care implement 100. More specifically, in the exemplified embodiment the tooth cleaning elements 111 extend from the front surface 122 of the head portion 120. A tongue or soft tissue cleaner (not depicted) may be positioned on the rear surface 123 of the head portion 120. Such a tongue or soft tissue cleaner may be formed of an elastomeric material and may include protrusions, nubs, ridges, scrapers, or the like for engaging and cleaning a user's oral tissue surfaces.

The term "tooth cleaning elements" is used in a generic sense to refer to any structure that can be used to clean, polish, or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. The tooth cleaning elements may include tapered bristles, non-tapered (i.e., end rounded) bristles, and combinations thereof. Any combination of the various types of tooth cleaning elements may be used on the oral care implement 100 in different embodiments. Thus, although the exemplified embodiment illustrates all of the tooth cleaning elements 111 as bristle filaments, the invention is not to be so limited in all embodiments and bristle filaments alone, a combination of bristle filaments and rubber bristles, rubber bristles alone, or other combinations of the different tooth cleaning element types identified above may be used.

In embodiments that use elastomeric/rubber elements as one or more of the tooth cleaning elements 111, suitable elastomeric materials may include any biocompatible resilient material suitable for uses in an oral hygiene apparatus. To provide optimum comfort as well as cleaning benefits, the elastomeric material of any such tooth or soft tissue engaging elements may have a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used. Although the exemplified embodiment illustrates the use of anchor-free tufting (AFT) for securing the tooth cleaning elements 111 to the head portion 120 of the body 101, the invention is not to be so limited in all embodiments. The tooth cleaning elements 111 may be coupled to the head portion 120 of the body 101 using any technique known in the art, such as stapling, AFT, in-mold tufting, AMR, or the like. The invention is not to be limited by the manner in which the tooth cleaning elements 111 are coupled to the head portion 120 in all embodiments, although some examples of specific tooth cleaning element coupling techniques will be discussed below with specific reference to FIGS. 3A and 3B.

Figure 2:
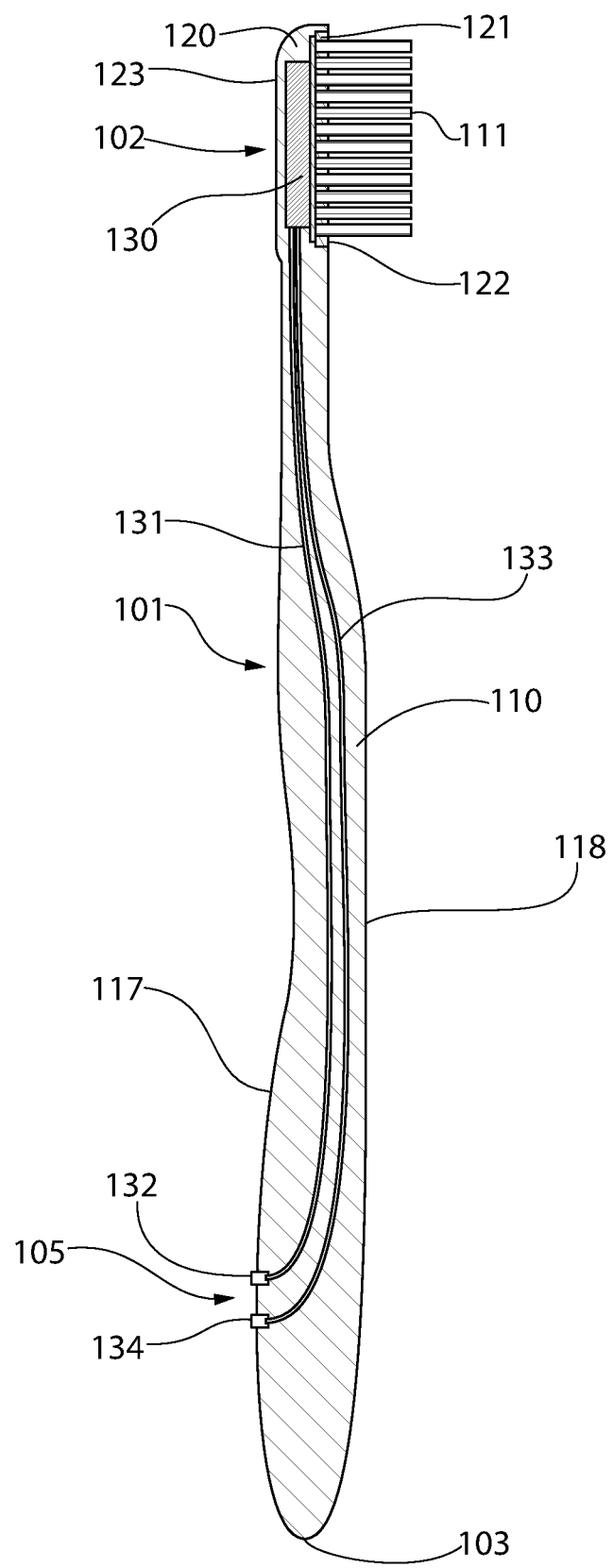
FIG. 2 is a cross-sectional view taken along line II-II of FIG. 1.

Referring to FIG. 2, the oral care implement 100 is illustrated in cross-section to describe some of the internal details of the oral care implement 100. The oral care implement 100 comprises a light source 130 located within the body 101. In the exemplified embodiment, the light source 130 is located within the head portion 120 of the body 101. However, the invention is not to be limited in this regard in all embodiments and the light source 130 may be positioned at other locations within the body 101 in other embodiments. However, there are advantages to placing the light source 130 within the head portion 120 of the body 101, such as ensuring that the light emitted from the light source 130 is directed at the tooth cleaning elements 111 to sanitize them.

The light source 130 may be configured to transmit ultraviolet (UV) light upon its activation by supplying power to the light source 130 as described in more detail herein below. Specifically, the light source 130 may transmit UVA, UVB, or UVC light as desired. In some instances UVA or UVB light may be preferable, and in other instances UVC light may be preferable due to its germicidal effects. When UVA or UVB (or even UVC) light is used, an enhancement material such as titanium dioxide ($TiO_2$), silver (Ag), zinc oxide (ZnO), or tin dioxide ($SnO_2$) may also be incorporated into the oral care implement 100 to increase the sanitizing effects of the UV light. In such embodiments, the light will pass through the enhancement material before reaching the tooth cleaning elements 111. UVC light is germicidal on its own, but an enhancement material may be used with UVC light to further increase the sanitizing effects in some embodiments. The use of an enhancement material will be described in greater detail with specific reference to FIGS. 14A and 14B.

The light source 130 is operably coupled to a first electrical coupling element 105, which in the exemplified embodiments includes a first electrical contact 132 and a second electrical contact 134. More specifically, the light source 130 is coupled to a first electrical conductor 131, which in turn is coupled to the first electrical contact 132. The light source is also coupled to a second electrical conductor 133, which in turn is coupled to the second electrical contact 134. In the exemplified embodiment each of the first and second electrical conductors 131, 133 is an electrical wire, but the invention is not to be so limited in all embodiments and other components known for electrical conductivity may be used. Other than the light source 130, the first and second electrical conductors 131, 133, and the first and second electrical contacts 132, 134, there are no further electrical components in the oral care implement 100. Specifically, there is no power source located within the oral care implement 100 (i.e., the oral care implement 100 is devoid or free of a power source). Thus, the oral care implement 100 is incapable, by itself, of supplying power to and activating the light source 130. Rather, the oral care implement, and specifically the first and second electrical contacts 132, 134 thereof, must be coupled to a separate device that has a power source to activate the light source 130 for sanitizing of the tooth cleaning elements 111.

The first and second electrical contacts 132, 134 may be referred to herein as a first pair of electrical contacts. This is because the first and second electrical contacts 132, 134 are both operably coupled to the light source 130 and both need to be coupled to a power source in order to activate the light source 130. Alternatively, the first and second electrical contacts 132, 134 may be collectively referred to herein as the first electrical coupling element 105. It should be appreciated that other types of electrical coupling elements may be used, such as inductive coils as described below with reference to FIGS. 13A and 13B. Thus, the term "electrical coupling element" may be used herein to refer to an electrical contact, a pair of electrical contacts, a coil used for inductive energy transfer, or similar.

In the exemplified embodiment, each of the first and second electrical contacts 132, 134 is located on a rear surface 117 of the handle portion 110 of the body 101. However, the invention is not to be so limited in all embodiments and the first and second electrical contacts 132, 134 may be located on a front surface 118 of the handle portion 110 of the body 101, or in other embodiments one of the first and second electrical contacts 132, 134 may be located on the front surface 118 of the handle portion 110 and the other of the first and second electrical contacts 132, 134 may be located on the rear surface 117 of the handle portion 110 (or on lateral surfaces of the body 101 between the front and rear surfaces 117, 118). The first and second electrical contacts 132, 134 may also be located on the rear surface 123 of the head portion 120 in some embodiments. In the exemplified embodiment the first and second electrical contacts 132, 134 are located near the proximal end 103 of the oral care implement 100 in a closely spaced apart manner, but greater spacing between the first and second electrical contacts 132, 134 and a location further up on the handle portion 110 closer to the head portion 120 or even within the head portion 120 is possible in other embodiments. Thus, the invention is not to be particularly limited by the location of the first and second electrical contacts 132, 134 in all embodiments.

In the exemplified embodiment, each of the first and second electrical contacts 132, 134 protrudes from the rear surface 117 of the handle portion 110 of the body 101. Thus, in the exemplified embodiment the first and second electrical contacts 132, 134 are exposed at the rear surface 117 of the handle portion 110 of the body 101. However, the invention is not to be so limited in all embodiments and in other embodiments the first and second electrical contacts 132, 134 may be flush with the rear surface 117 of the handle portion 110 of the body 101 or may be recessed relative to the rear surface 117 of the handle portion 110 of the body 101. It may in fact be preferable to recess the first and second electrical contacts 132, 134 relative to the surface (rear or front) of the body 101 at which they are located to prevent water or other fluids from contacting the first and second electrical contacts 132, 134 and possibly preventing their effective functionality in activating the light source 130. Furthermore, making them flush or recessed with the rear surface 117 of the handle portion 110 rather than protruding therefrom increase grip comfort during use.

Figure 3A:
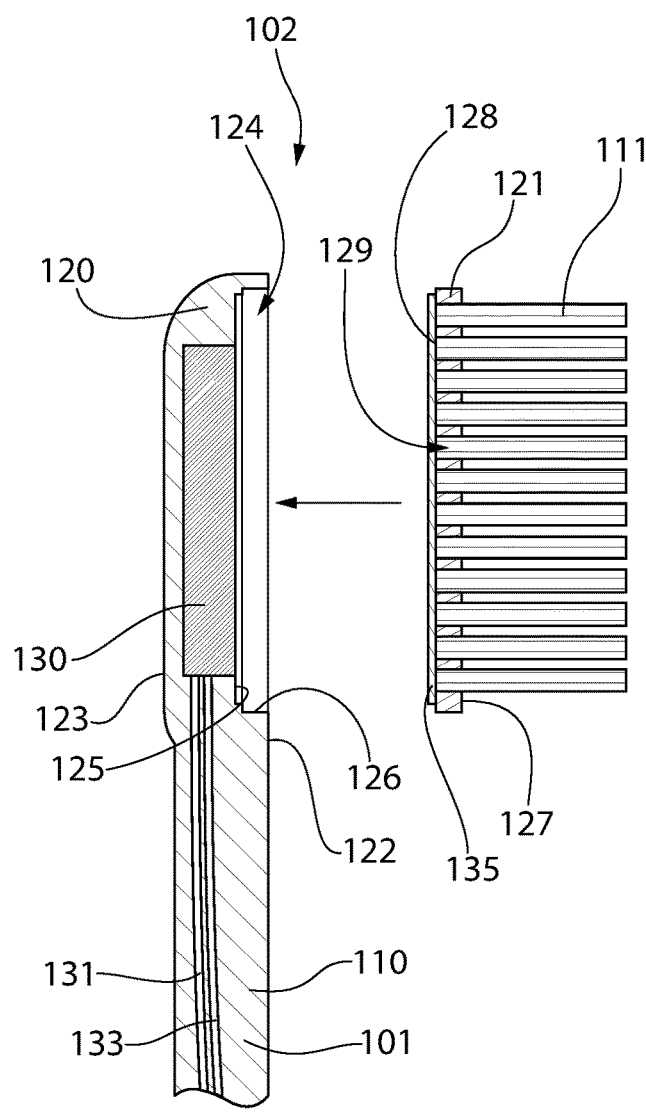
FIG. 3A is a close-up cross-sectional view of a head portion of the oral care implement of FIG. 2 with a head plate exploded away.
Figure 3B:
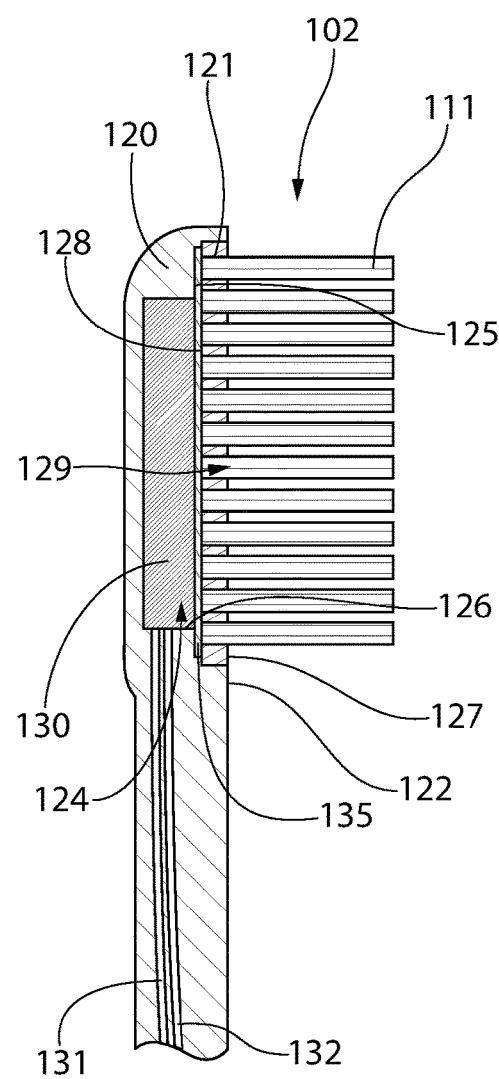
FIG. 3B is a close-up view of the head portion of the oral care implement of FIG. 2 with the head plate coupled to the head portion.

Referring now to FIGS. 3A and 3B concurrently, the structure of the head 102 will be described in greater detail. The head portion 120 of the body 101 comprises a basin 124 defined by a floor 125 and sidewalls 126 extending upwardly from the floor 125 to the front surface 122 of the head portion 120. In the exemplified embodiment, the light source 130 is embedded within the head portion 120 and forms a portion of the floor 125 of the basin 124. However, the invention is not to be so limited in all embodiments and in other embodiments the light source 130 may be located entirely between the floor 125 and the rear surface 123 of the head portion 120 without forming any part of the floor 125. In still other embodiments the light source 130 may be located within the basin 124 between the floor 125 and the front surface 122 of the head portion 120.

As discussed above, the head 102 also includes the head plate 121 which is coupled to the head portion 120 of the body 101 to form the fully formed head 102. The head plate 121 comprises a front surface 127 and an opposite rear surface 128. Furthermore, the head plate 121 comprises holes 129 that extend through the head plate 121 from the front surface 127 of the head plate 121 to the rear surface 128 of the head plate 121. During manufacturing, the tooth cleaning elements 111 are bundled together into tufts, and each of the tufts is inserted into one of the tuft holes 129 so that a first portion of the tufts protrudes from the front surface 127 of the head plate 121 and a second portion of the tufts protrudes from the rear surface 128 of the head plate 121. The first portion of the tufts is used for contacting a user's oral surfaces. The second portion of the tufts are melted by heat and then allowed to cool, thereby forming a layer on the rear surface 128 of the head plate 121 that is known as a melt mat 135. The melt mat 135 is positioned adjacent to the rear surface 128 of the head plate 120 and prevents the tooth cleaning elements 111 from being pulled through the holes 129 in a direction of the front surface 127 of the head plate 121.

As shown in FIG. 3B, in the fully formed oral care implement 100, the head plate 121 is inserted into the basin 124 of the head portion 120 of the body 101 and coupled thereto using techniques known in the art such as ultrasonic welding, adhesion, interference fit, or the like. When the head plate 121 is inserted into the basin 124, the melt mat 135 becomes trapped between the rear surface 128 of the head plate 121 and the floor 125 of the basin 122. This effectively secures the tooth cleaning elements 111 to the head 102 and prevents them from being separated therefrom.

In the exemplified embodiment, the head plate 121 is positioned within the basin 124 so that the light source 130 is adjacent to the melt mat 135. More specifically, in the exemplified embodiment the light source 130 is in direct surface contact with the melt mat 135, although this is not required in all embodiments and a space between the melt mat 135 and the light source 130 may be provided in other embodiments. In some embodiments the tooth cleaning elements 111, and hence also the melt mat 135 which is formed from the tooth cleaning elements 111, may be formed of a light transmissive material (i.e., transparent or translucent) to facilitate transmission of the light emitted from the light source through the melt mat 135 and into the tooth cleaning elements 111 to achieve effective sanitization thereof. Bacteria are most likely to grow in wet environments, such as the base/root of the tooth cleaning elements 111 near the melt mat 135. Thus, positioning the light source 130 as illustrated ensures that the UV light emitted from the light source 130 will contact those regions of the tooth cleaning elements 111 that are most prone to bacterial growth.

Although the exemplified embodiment shows the head 102 being formed from the head portion 120 of the body 101 and the head plate 121 using an AFT technique, the invention is not to be so limited in all embodiments. In some alternative embodiments that are not illustrated herein, the head 102 may be a single unitary structure such that the head plate 121 is omitted and such that the head portion 120 does not have a basin. In such embodiment, the head portion 120 may have tuft holes therein, and the tooth cleaning elements 111 may be inserted into the tuft holes in the head portion 120 and secured thereto using staples as is known in the art. Thus, any known technique for securing the tooth cleaning elements 111 to the head 102 may be used in accordance with the present invention and the invention is not to be particularly limited in this regard in all embodiments.

Figure 4:
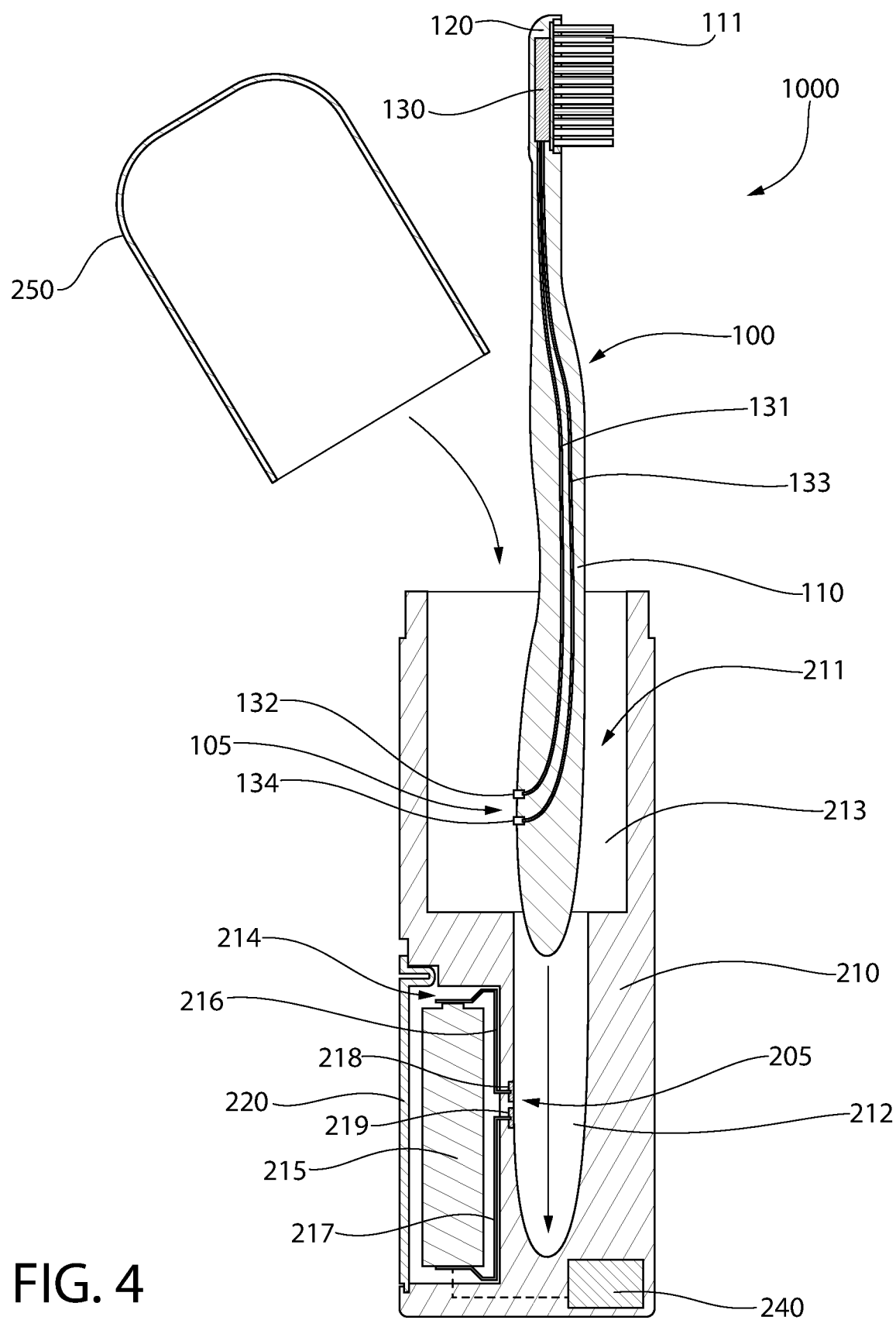
FIG. 4 is a schematic view of an oral care implement being inserted into a case in accordance with a first embodiment of the present invention.

Referring to FIG. 4, an oral care implement sanitization system 1000 is illustrated in accordance with an embodiment of the present invention. The oral care implement sanitization system 1000 generally comprises the oral care implement 100 described above and a case 200 for storing the oral care implement 100 and activating the light source 130. The case 200 generally comprises a housing 210 and a cover 250. The housing 210 comprises a cavity 211 for holding the oral care implement 100. The cavity 211 has an open top end 221 through which the oral care implement 100 can be inserted into and removed from the cavity 211. The cover 250 can be coupled to the housing 210 to close the open top end 221 of the cavity 211. In the exemplified embodiment, the cover 250 is a separate component from the housing 210 that may be coupled to the housing 210 to enclose the cavity 211. However, in other embodiments the cover 250 may be always coupled to the housing (such as via a hinge) but alterable between a first state in which the cavity 211 is open (i.e., the open top end 221 is not closed) and a second state in which the open top end 221 of the cavity 211 is closed by the cover 250.

The cavity 211 of the housing 210 comprises a first portion 212 configured to retain a first portion of the oral care implement 100 and a second portion 213 configured to retain a second portion of the oral care implement 100. In certain embodiments, the first portion 212 of the cavity 211 may operate as an alignment member to only permit the oral care implement 100 to be inserted into the cavity 211 in a specific orientation designed to ensure that power is supplied to the light source 130 as described in greater detail below. This can be accomplished, by way of example without limitation, by forming the first portion 212 of the cavity 211 with a cross-sectional shape that corresponds to a cross-sectional shape of the handle portion 110 of the body 101 or by having corresponding protrusions and recesses on the first portion 212 of the cavity 211 and the handle portion 110 of the body 101.

The housing 210 comprises a compartment 214 for holding a power source 215, which in the exemplified embodiment is a battery. Although a battery is illustrated, the invention is not to be so limited and any type of power source may be used. The compartment 214 is closed by a door 220 that can be opened to provide a user with access to the power source 215 for replacement thereof as necessary. The compartment 214 is separated from the cavity 211 such that any fluid that enters into the cavity 211 will not be able to penetrate into the compartment 214. The door 220 also helps to prevent fluids from entering into the compartment 214. This is to protect the power source 215 against water damage that may destroy its ability to supply power to the light source 130 in the oral care implement 100.

The power source 215 is operably coupled to a second electrical coupling element 205. More specifically, in the exemplified embodiment, located within the compartment 214 of the case 200 is a first electrical conductor 216 configured to be coupled to the cathode or positive terminal of the power source 215 and a second electrical conductor 217 configured to be coupled to the anode or negative terminal of the power source 215. Furthermore, the first electrical conductor 216 is operably coupled to a first electrical contact 218 and the second electrical conductor 217 is operably coupled to a second electrical contact 219. The first and second electrical contacts 218, 219 collectively form the second electrical coupling element 205 and may be referred to herein as a second pair of electrical contacts. In the exemplified embodiment, the first and second electrical contacts 218, 219 of the case 200 are operably coupled to the power source 215 via the first and second electrical conductors 216, 217. However, the first and second electrical contacts 218, 219 are spaced apart from one another.

In the exemplified embodiment, the case 200 further comprises a processor 240 operably coupled to the power source 215. The processor 240 may include its own separate power source for powering the processor 240 or the power source 215 may provide power to the processor 240. The processor 240 may be configured to control operation of the power source 115. For example, the processor 240 may include a timing circuit such that the processor 240 only permits the power source 115 to provide power to the light source 130 for a predetermined period of time before stopping the power source 115 from providing power to the light source 130 to control the length of time that the light source 130 emits light. The processor 240 is not required in all embodiments and it may be omitted in some embodiments particularly where control of the activation time of the light source 130 is not needed or desired.

Figure 5:
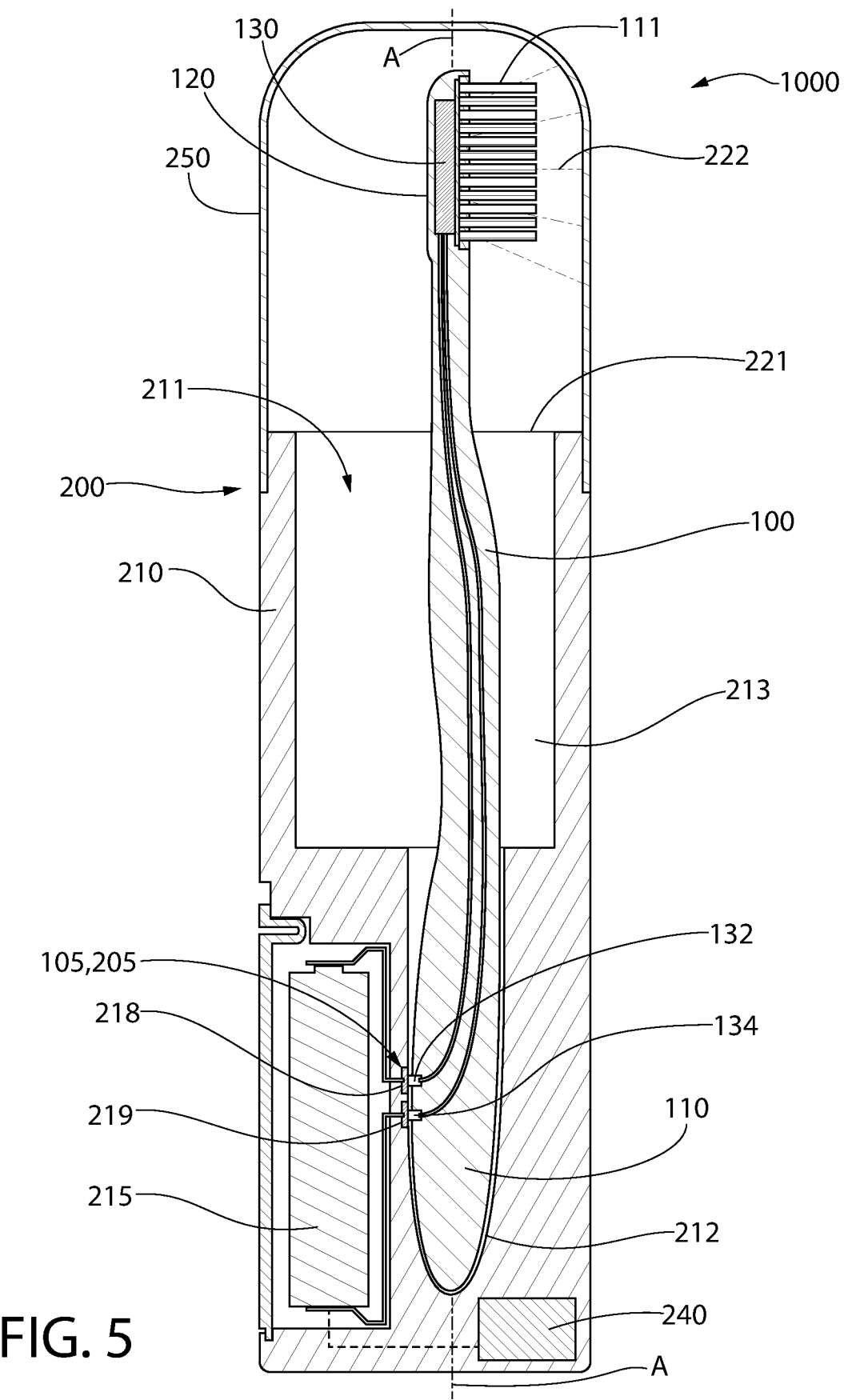
FIG. 5 is a schematic view of the embodiment of FIG. 4 with the oral care implement fully inserted into the case.

FIG. 5 illustrates the oral care implement sanitization system 1000 with the oral care implement 100 fully inserted into the cavity 211 of the case 200. When the oral care implement 100 is inserted into the cavity 211 of the case 200, first and second electrical coupling elements 105, 205 are operably coupled together. In the exemplified embodiment, this is achieved by operably coupling the first pair of electrical contacts 132, 134 of the oral care implement 100 to the second pair of electrical contacts 218, 219 of the case 200. Specifically, the first electrical contact 132 of the oral care implement 100 is operably coupled to the first electrical contact 218 of the case 200 and the second electrical contact 134 of the oral care implement 100 is operably coupled to the second electrical contact 219 of the case 200. This coupling of the first and second pairs of electrical contacts 132, 134, 218, 219 forms a closed circuit between the power source 215 and the light source 130, thereby activating the light source 130. Specifically, when the first electrical contact 132 of the first pair is coupled to the first electrical contact 218 of the second pair and the second electrical contact 134 of the first pair is coupled to the second electrical contact 219 of the second pair, the light source 130 may be automatically activated to transmit UV light 222 to the tooth cleaning elements 111. Thus, when the first and second pairs of electrical contacts 132, 134, 218, 219 are electrically coupled to one another, the light source 130 is activated and transmits UV light 222 towards the tooth cleaning elements 111.

In FIG. 5, the cover 250 is illustrated coupled to the housing 210 of the case 200. The cover 250 and the housing 210 collectively circumferentially surround the oral care implement 100 along its entire length. Thus, with the oral care implement 100 within the cavity 211 and the cover 250 coupled to the housing 210, no portion of the oral care implement 100 is exposed. Stated another way, the housing 210 and the cover 250 collectively form a fully enclosed volume of space, and the oral care implement 100 is entirely located within the enclosed volume of space. In the exemplified embodiment, the housing 210 circumferentially surrounds a majority of the length of the handle portion 110 of the body 101 and the cover 250 circumferentially surrounds the remainder of the handle portion 110 of the body 101 and the head portion 120 of the body 101. Of course, the relative sizes of the housing 210 and the cover 250 may be adjusted/changed in some embodiments. For example, in some embodiments the housing 210 may surround the oral care implement 100 along its entire length and the cover 250 may be a flat cap that just closes the open top end 221 of the housing 210 without circumferentially surrounding any portion of the oral care implement 100.

Although in the exemplified embodiment the case 200 encloses the entirety of the oral care implement 100, the invention is not to be so limited in all embodiments. In other embodiments the case 200 may only enclose the head portion 120 of the oral care implement 100 including the tooth cleaning elements 111. In certain embodiments the head portion 120 may be detachable from the handle portion 110, and the case 200 may enclose the head portion 120 when it is separated from the handle portion 110. Alternatively, the handle portion 110 and the head portion 120 may both be stored in the case 200, but in the detached state, while still accomplishing the inventive concepts described herein.

In certain embodiments, the cover 250 may be formed of an opaque material or may otherwise be formed of a material that the UV light 222 cannot pass through. Thus, the UV light 222 may be transmitted towards the tooth cleaning elements 111 but the cover 250 prevents a user from being exposed to the UV light 222. The UV light 222 transmitted from the light source 130 sanitizes the tooth cleaning elements 111 by killing bacteria and germs and preventing their growth. A wet environment is typically required for bacterial growth. Thus, bacterial growth is most prevalent in the root of the tooth cleaning elements 111, because the portions of the tooth cleaning elements 111 that are spaced from the head are better able to dry over time. Thus, it is preferable to direct/focus the UV light 222 at the root of the tufts of bristles to prevent bacterial growth.

As noted above, in certain embodiments activation of the light source 130 may be automatic and may continue for a predetermined period of time before automatically shutting off. The processor 240 may be configured to achieve this functionality. Specifically, in certain embodiments as soon as the first and second electrical coupling elements 105, 205 (i.e., the electrical contacts 132, 134, 218, 219) are operably coupled together, the light source 130 is automatically activated to transmit the UV light 222 for a predetermined period of time (i.e., five minutes, ten minutes, or any other desired time). After expiration of the predetermined period of time, the processor 240 will cause the power source 215 to stop supplying power to the light source 130, thereby terminating transmission of the UV light from the light source 130 to the tooth cleaning elements 111. Thus, the processor 240 may be configured to activate the light source 130 for a predetermined period of time and to then automatically deactivate the light source 130 after expiration of the predetermined period of time. However, the invention is not to be so limited in all embodiments and in other embodiments a user may be required to adjust a manual switch to activate and deactivate the light source 130 when the necessary electrical connection is made between the electrical contacts 132, 134, 218, 219 of the oral care implement 100 and the case 200. Such a switch may be positioned at a location on the oral care implement 100 or on the case 200.

Figure 6:
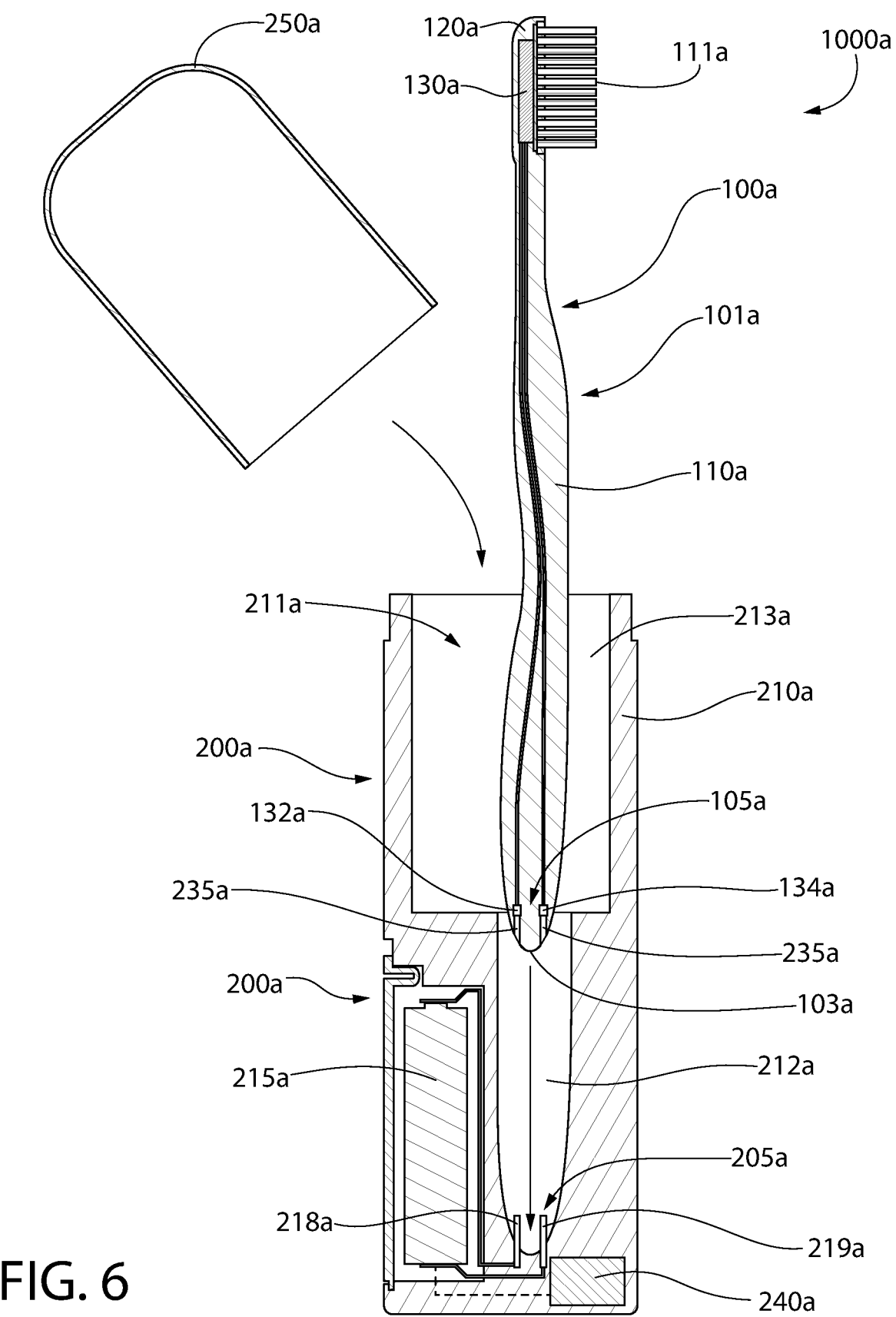
FIG. 6 is a schematic view of the oral care implement being inserted into a case in accordance with a second embodiment of the present invention.
Figure 7:
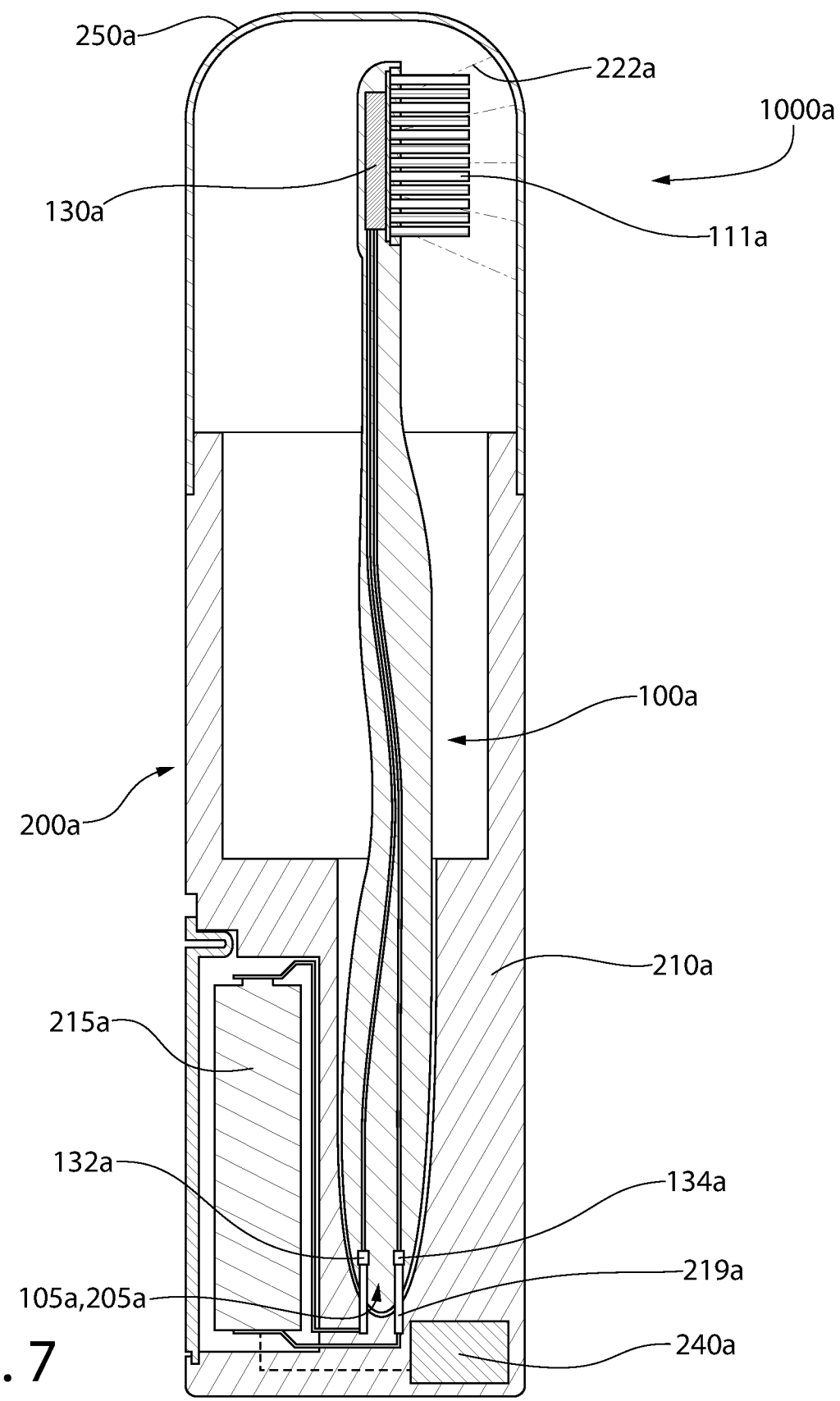
FIG. 7 is a schematic view of the embodiment of FIG. 6 with the oral care implement fully inserted into the case.

Referring to FIGS. 6 and 7, an alternative oral care implement sanitization system 1000a is illustrated in accordance with an embodiment of the present invention. The oral care implement sanitization system 1000a generally comprises an oral care implement 100a and a case 200a. Only the differences between the oral care implement 100a and the oral care implement 100 described above and the differences between the case 200a and the case 200 described above will be discussed herein below. It should be appreciated that except as provided herein below, the description of the oral care implement 100 and the case 200 is applicable to this embodiment. The features of the oral care implement 100a and the case 200a will be similarly numbered to the features of the oral care implement 100 and the case 200 except that the suffix "a" will be used. Thus, for features of the oral care implement 100a and the case 200a that are numbered in the drawings but not described, the similarly numbered feature of the oral care implement 100 and the case 200 is applicable.

In this embodiment, the first and second electrical contacts 132a, 134a of the first electrical coupling element 105a are located at the proximal end 103a of the handle portion 110a of the body 101a. Furthermore, the first and second electrical contacts 132a, 134a are recessed relative to the outer surface of the body 101a. Thus, the first and second electrical contacts 132a, 134a are fairly well protected against contact with water and are recessed so that they do not disturb a user's grip during use. A channel 235a is formed into the oral care implement 100a and extends from the proximal end 103a of the oral care implement 100a inwardly to the first and second electrical contacts 132a, 134a.

The first and second electrical contacts 218a, 219a of the second electrical coupling element 205a are located in the bottom portion of the first portion 212a of the cavity 211a to ensure that when the oral care implement 100a is inserted into the cavity 211a, the first and second electrical contacts 218a, 219b of the case 200a come into contact with the first and second electrical contacts 132a, 134a of the oral care implement 100a. FIG. 6 illustrates the system with the oral care implement 100a ready for insertion into the case 200a. FIG. 87 illustrates the system with the oral care implement 100a fully inserted into the cavity 211a of the case 200a. As can be seen in FIG. 7, when the oral care implement 100a is inserted into the cavity 211a of the case 200a, the first pair of electrical contacts 132a, 134a of the oral care implement 100a come into contact with the second pair of electrical contacts 218a, 219a of the case 200a, which in turn causes activation of the light source 130a. More specifically, the electrical contacts 218a, 219a of the case 200a pass into the channels 235a to make contact with the electrical contacts 132a, 134a of the oral care implement 100a. The cover 250a can be coupled to the housing 210a to fully enclose the oral care implement 100a and prevent or minimize user exposure to the UV light.

Figure 8:
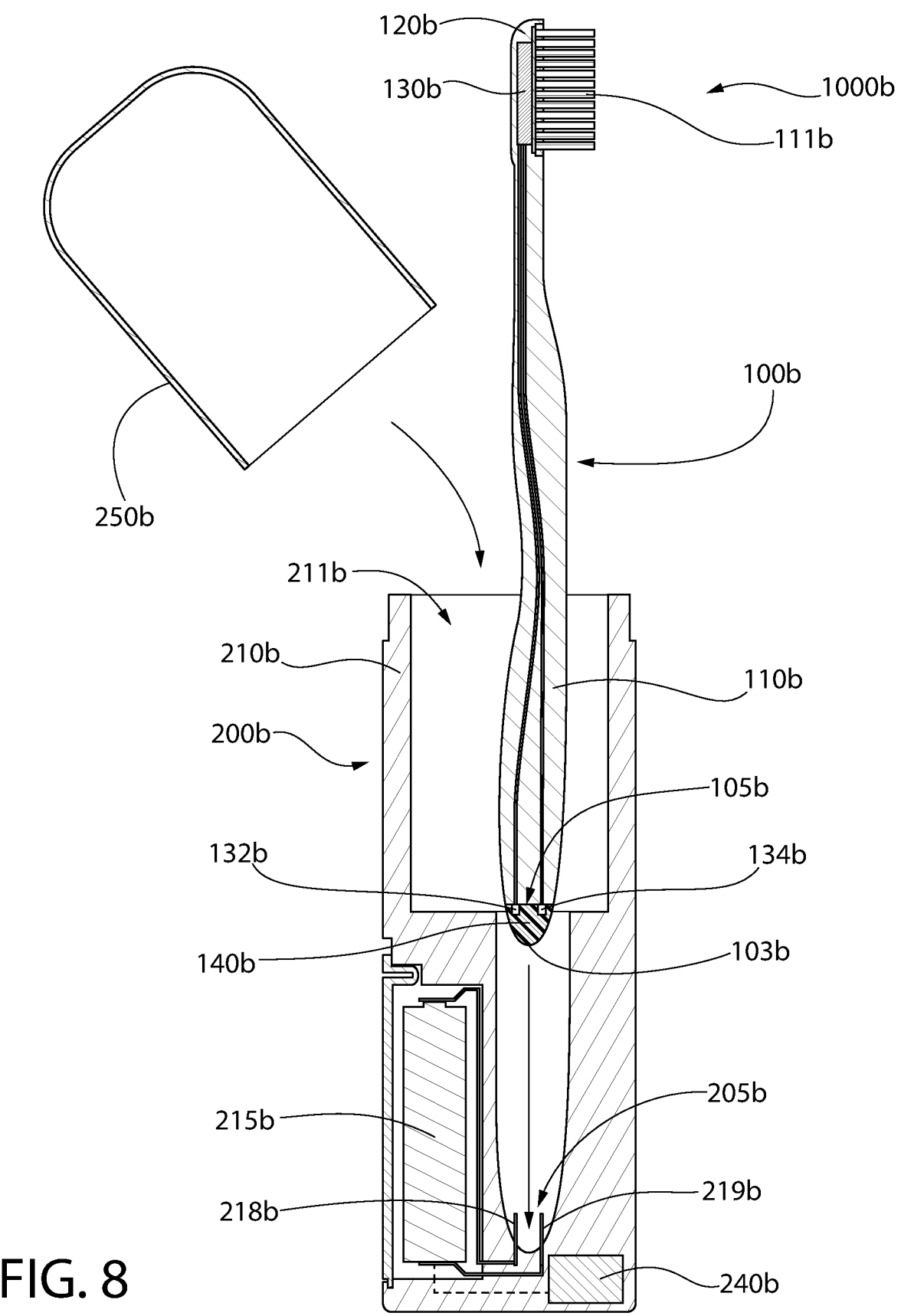
FIG. 8 is a schematic view of an oral care implement being inserted into a case in accordance with a third embodiment of the present invention.
Figure 9:
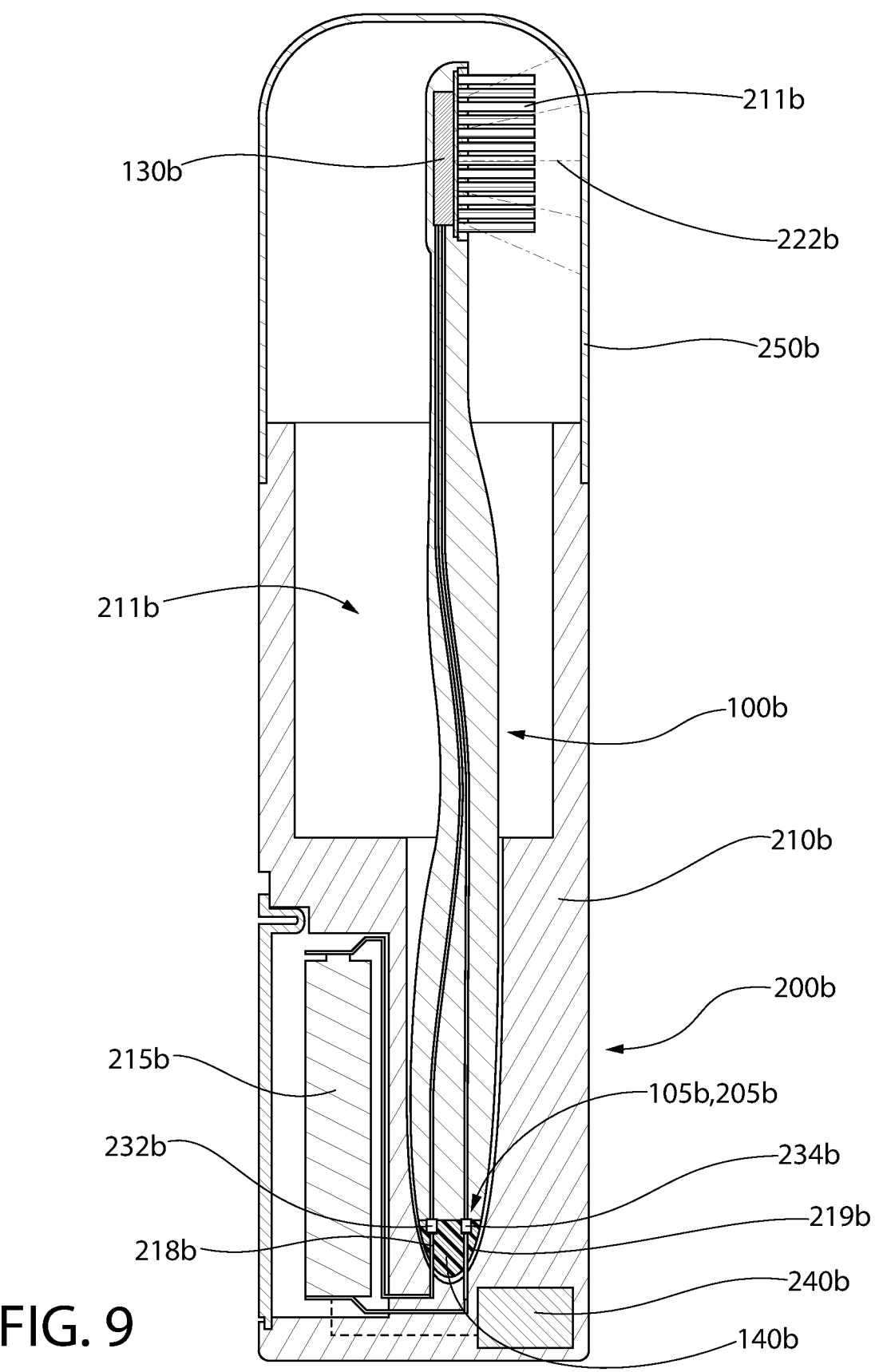
FIG. 9 is a schematic view of the embodiment of FIG. 8 with the oral care implement fully inserted into the case.

Referring to FIGS. 8 and 9, an alternative an oral care implement sanitization system 1000b is illustrated in accordance with an embodiment of the present invention. The oral care implement sanitization system 1000b generally comprises an oral care implement 100b and a case 200b. Only the differences between the oral care implement 100b and the oral care implement 100 described above and the differences between the case 200b and the case 200 described above will be discussed herein below. It should be appreciated that except as provided herein below, the description of the oral care implement 100 and the case 200 is applicable to this embodiment. The features of the oral care implement 100b and the case 200b will be similarly numbered to the features of the oral care implement 100 and the case 200 except that the suffix "a" will be used. Thus, for features of the oral care implement 100b and the case 200b that are numbered in the drawings but not described, the similarly numbered feature of the oral care implement 100 and the case 200 is applicable.

In this embodiment, the first and second electrical contacts 132b, 134b of the first electrical coupling element 105b of the oral care implement 100 are located at the proximal end 103b of the oral care implement 100b, although other locations for the first and second electrical contacts 132b, 134b are within the scope of this embodiment as well. The main difference in this embodiment is that the first and second electrical contacts 132b, 134b are covered by an elastomeric material 140b. Although in this embodiment the elastomeric material 140b forms the proximal end 103b of the oral care implement 100b, this is not required in all embodiments. The first and second electrical contacts 132b, 134b could be located on the front or rear surface of the handle portion 110b of the oral care implement 100b and the elastomeric material 140b could simply cover them wherever they are located. Thus, the elastomeric material 140b may have a dual function of providing protection to the first and second electrical contacts 132b, 134b and forming a gripping surface that is overlaid onto the handle portion 110b to enhance gripability during use.

As seen in FIG. 9, when the oral care implement 100b is placed into the cavity 211b of the case 200b, the first and second electrical contacts 218b, 219b of the second electrical coupling element 205c of the case 200b extend through the elastomeric material 140 to make contact with the first and second electrical contacts 132b, 134b of the oral care implement 100b to supply power to the light source 130b so that it generates UV light 222b. The first and second electrical contacts 218b, 219b of the case 200b may have pointed ends to enable them to pass through the elastomeric material 140b. Alternatively, the elastomeric material 140b may be formed with small passageways. Due to the compressibility of the elastomeric material 140, when the oral care implement 100b is inserted into the cavity 211b, the first and second electrical contacts 218b, 219b of the case 200b will enter into the passageways of the elastomeric material 140b to enable the first and second electrical contacts 218b, 219b of the case 200b to make contact with the first and second electrical contacts 132b, 134b of the oral care implement 100b. The malleability of the elastomeric material 140b assists in enabling the electrical contacts 218b, 219b to pass therethrough. Thus, the elastomeric material 140b will separate in the region of the passageways when the oral care implement 100b is being inserted into the cavity 211b as the electrical contacts 218b, 219b of the case 200b engage the elastomeric material 140b. Furthermore, the elastomeric material 140b will compress itself to substantially close the passageways when the oral care implement 100b is removed from the cavity 211b of the case 200b and the electrical contacts 218b, 219b of the case 200b disengage from the elastomeric material 140b.

Figure 10:
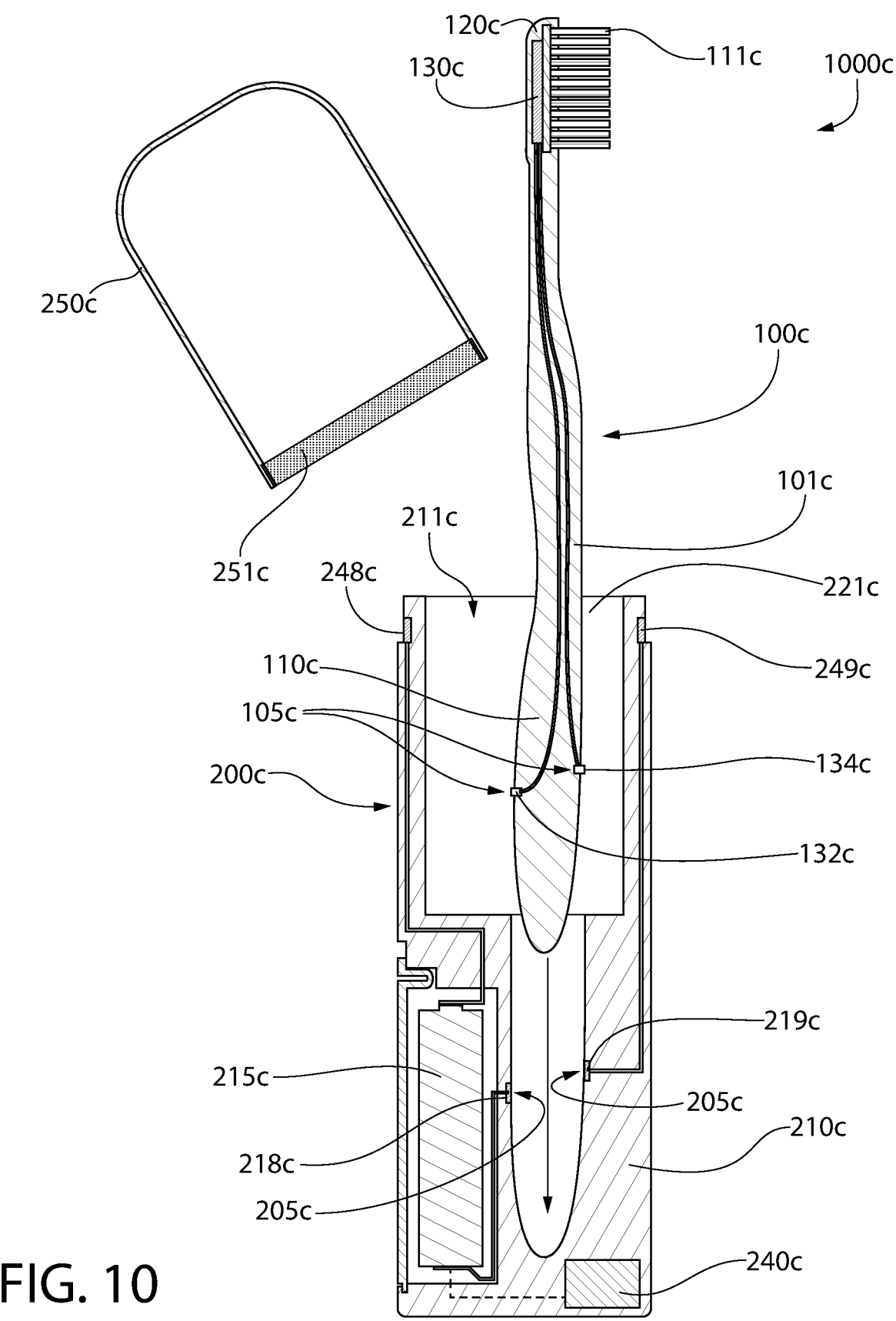
FIG. 10 is a schematic view of an oral care implement being inserted into a case in accordance with a fourth embodiment of the present invention.
Figure 11:
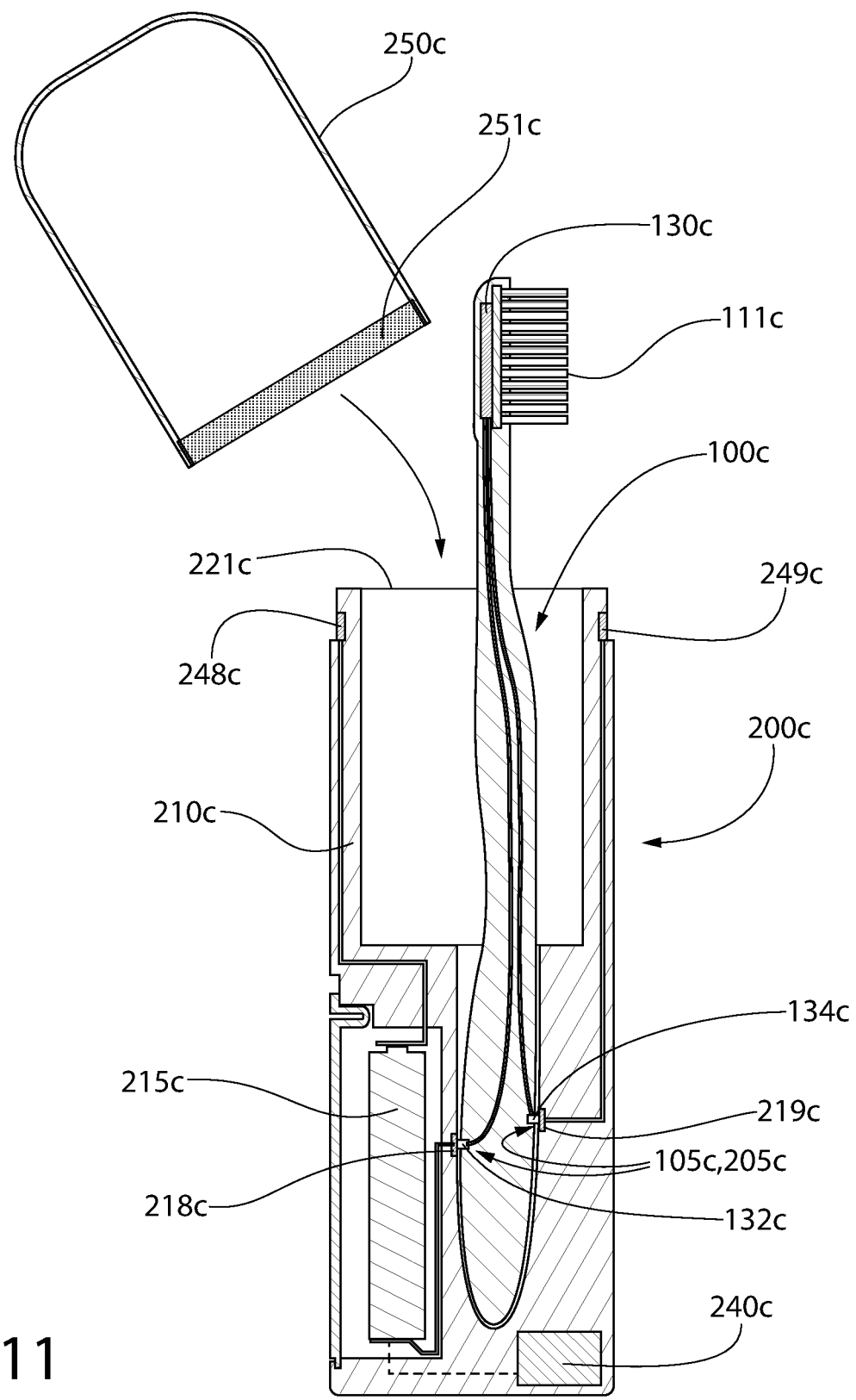
FIG. 11 is a schematic view of FIG. 10 with the oral care implement fully inserted into the case and a cover separated from a housing of the case.
Figure 12:
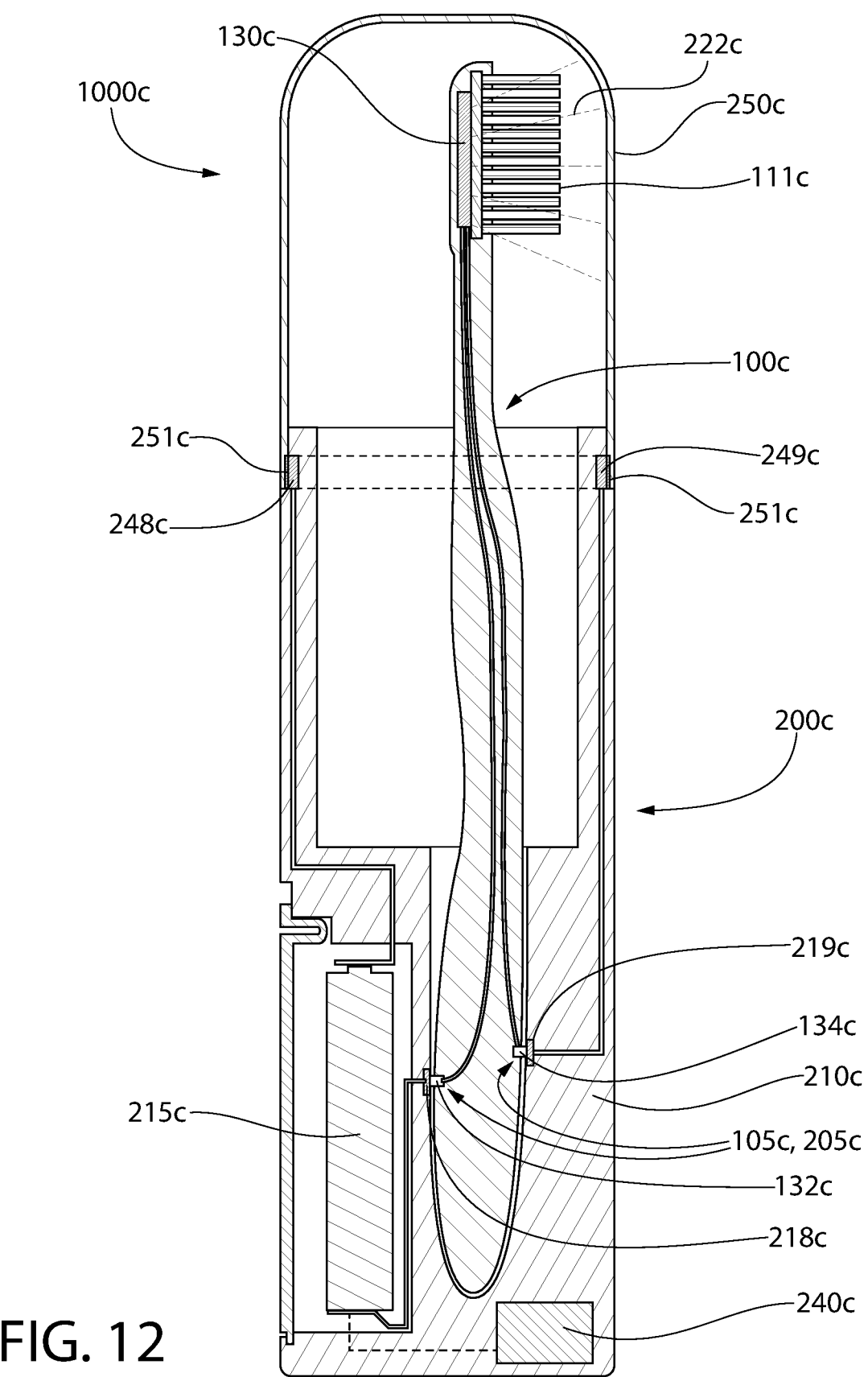
FIG. 12 is a schematic view of FIG. 11 with the cover coupled to the housing of the case.

FIGS. 10-12 illustrate yet another embodiment of an oral care implement sanitization system 1000c. Features of the oral care implement sanitization system 1000c that are similar to features of the oral care implement sanitization system 1000 described above with regard to FIGS. 4 and 5 will be similarly numbered except that the suffix "c" will be used. It should be appreciated that for features of the oral care implement sanitization system 1000c that are numbered but not described, the description of the similar feature with regard to the oral care implement sanitization system 1000 is applicable.

The oral care implement sanitization system 1000c generally comprises an oral care implement 100c and a case 200c. The oral care implement 100c comprises a body 101c having a handle portion 110c and a head portion 120c. The head portion 120c comprises a plurality of tooth cleaning elements 111c and a light source 130c. The oral care implement 100c further comprises a first electrical coupling element 105c, which in the exemplified embodiment comprises a first electrical contact 132c and a second electrical contact 134c, each of which is operably coupled to the light source 130c. In the exemplified embodiment the first electrical contact 132c is located on a rear surface of the handle portion 110c and the second electrical contact 134c is located on a front surface of the handle portion 110c. However, the invention is not to be so limited in all embodiments and the first and second electrical contacts 132c, 134c may be positioned at other locations along the oral care implement 100c such as that which has been described above.

The case 200c generally comprises a housing 210c and a cover 250c. The housing 210c comprises a cavity 211c having an open top end 221c. Furthermore, the housing 210c contains a power source 215c and a second electrical coupling element 205c, which in the exemplified embodiment comprises first and second electrical contacts 218c, 219c. In this embodiment, the first electrical contact 218c is coupled to the power source 215c and the second electrical contact 219c is not coupled to the power source 215c. In other embodiments, the second electrical contact 219c may be coupled to the power source 215c and the first electrical contact 218c may not be coupled to the power source. This is done so that the light source 130c is not automatically activated upon the oral care implement 100c being disposed within the cavity 211c. Specifically, even when the first and second electrical contacts 132c, 134c of the oral care implement 100c are operably coupled to the first and second electrical contacts 218c, 219c of the case 200c (FIG. 11), the circuit that includes the power source 215c and the light source 130c remains open so no power is transmitted to the light source 130c.

In the exemplified embodiment, the housing 210c of the case 200c comprises a third electrical coupling element (or third electrical contact) 248c that is operably coupled to the power source 215c and a fourth electrical coupling element (or fourth electrical contact) 249c that is operably coupled to the second electrical contact 219c. Thus, the first and third electrical contacts 218c, 248c are operably coupled to the power source 215c and the second and fourth electrical contacts 219c, 249c are operably coupled to each other but not to the power source 215c.

The cover 250c closes the open top end 221c of the cavity 211c when the cover 250c is coupled to the housing 210c. In the exemplified embodiment, the cover 250c comprises a metal ring 251c that functions as an electrical coupling element or electrical contact for closing the circuit between the power source 215c and the light source 130c as discussed in more detail below. Although a metal ring 251c is used in the exemplified embodiment, other structures, features, or the like could be used in other embodiments to close the circuit to enable activation of the light source 130c.

FIG. 11 illustrates the oral care implement sanitization system 1000c with the oral care implement 100c positioned within the cavity 211c of the case 200c but with the cover 250c separated from the housing 210c (or otherwise not covering the open top end 221c of the housing 210c). When the oral care implement 100c is inserted into the cavity 211c, the first electrical contact 132c of the oral care implement 100c is operably coupled to the first 218c electrical contact 218c of the case 200c and the second electrical contact 134c of the oral care implement 100c is operably coupled to the second electrical contact 219c of the case 200c. However, in this state the light source 130c remains deactivated because the circuit between the power source 215c and the light source 130c is still open. The third and fourth electrical contacts 248c, 249c need to be electrically coupled to one another to close the circuit and activate the light source 130c.

FIG. 12 illustrates the oral care implement sanitization system 1000c with the oral care implement positioned within the cavity 211c of the case 200c and with the cover 250c coupled to the housing 210c. When the cover 250c is coupled to the housing 210c, the metal ring 251c of the cover 250c becomes operably coupled to both the third and fourth electrical contacts 248c, 249c of the housing 210c, thereby electrically coupling the third and fourth electrical contacts 248c, 249c to each other. This coupling between the metal ring 251c of the cover 250c and the third and fourth electrical contacts 248c, 249c of the housing 210c closes the circuit and permits power to be transmitted from the power source 215c to the light source 130, thereby activating the light source 130c to generate/transmit UV light 222c.

Thus, in this embodiment the light source 130c is unable to emit the UV light 222c until the cover 250c is coupled to the housing 210c to close the open top end 221c of the cavity 211c of the housing 210c. This ensures that the cover 250c is properly in place before the light source 130c begins to transmit the UV light 222c. Thus, in embodiments where the cover 250c is impenetrable to the UV light 222c, the user is protected from the UV light rays because the UV light rays are only generated when the cover 250c is in place. In all of the above described embodiments, the processor 240c may be used as a timing circuit to ensure activation of the light source 130c is achieved automatically upon the circuit being closed and continues for a predetermined period of time before being automatically deactivated as described above.

In any of the embodiments described herein, the cover 250c may be formed of an opaque material as described previously, or it may be formed of a transparent material or comprise a section that is formed of a transparent material so that a user can tell that the light source 130c is activated. Specifically, the cover 250c may include a window that permits a user to see that the light source 130c is activated without placing the user in danger due to the UV light. Alternatively, the cover 250c may include a fluorescing or phosphorescing material incorporated therein that is excited by the UV light transmitted by the light source 130C. This would provide another technique for indicating to the user that the light source 130c is activated by visualization of the excitation of the fluorescing or phosphorescing material in the cover 250c.

Figure 13A:
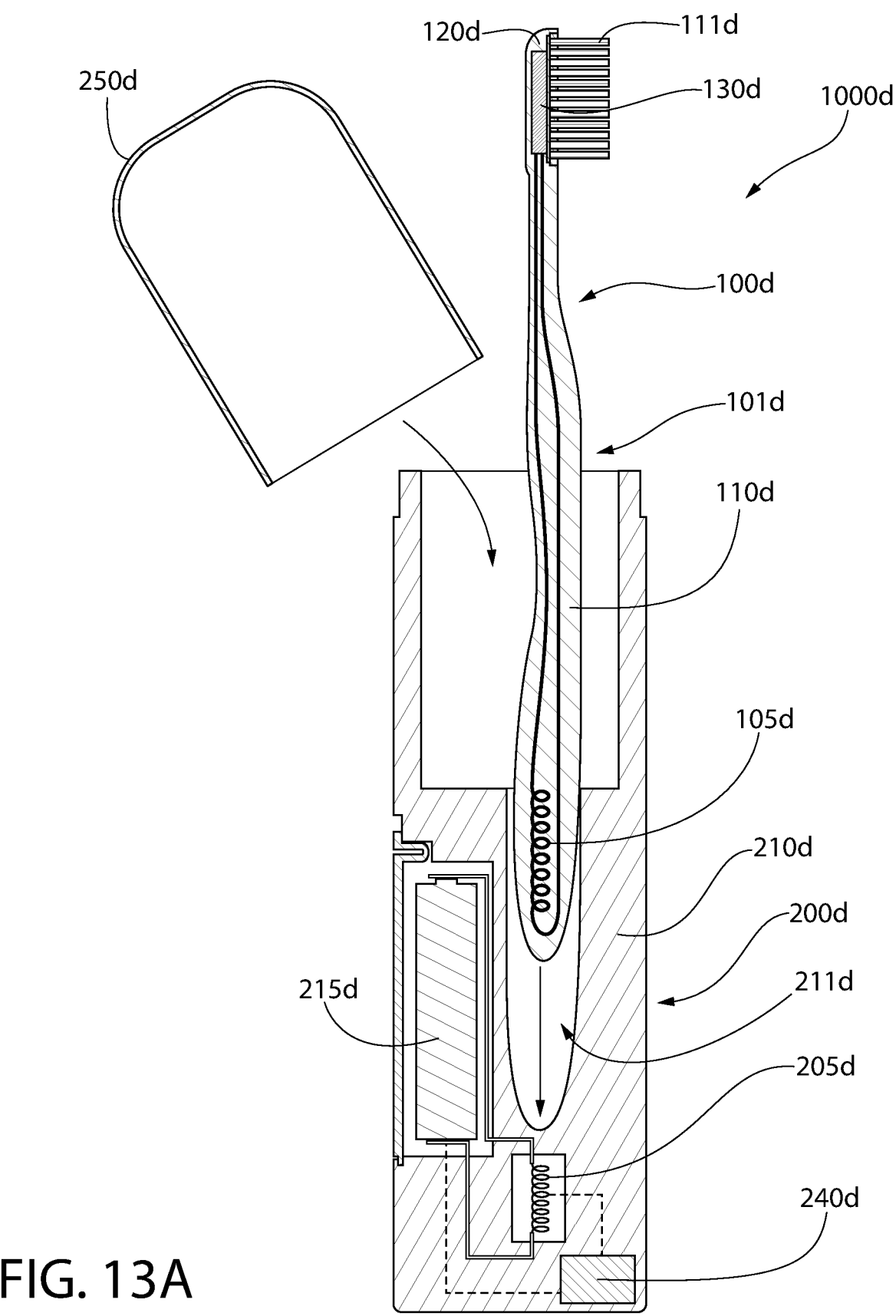
FIG. 13A is a schematic view of an oral care implement being inserted into a case in accordance with a fifth embodiment of the present invention.
Figure 13B:
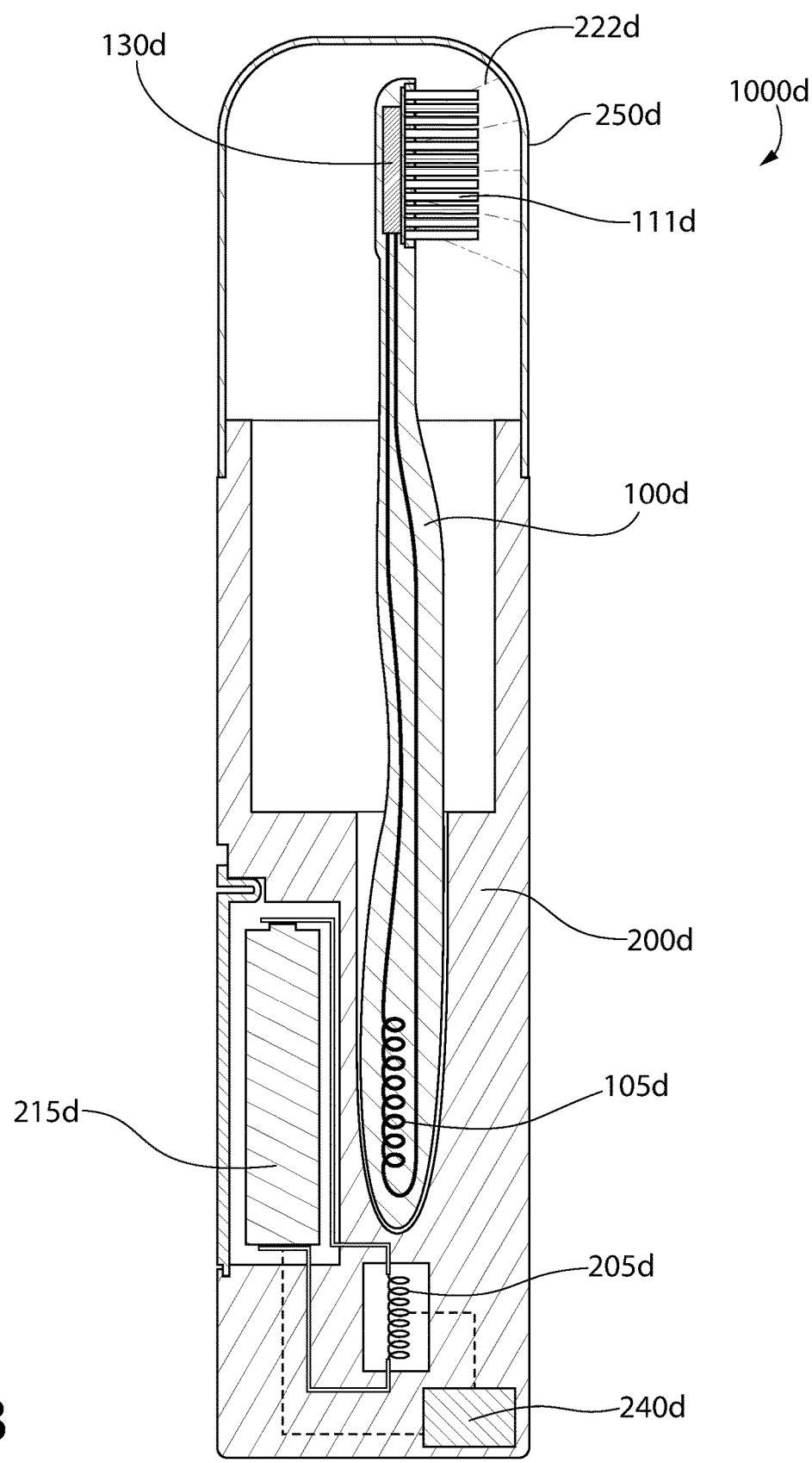
FIG. 13B is a schematic view of the embodiment of FIG. 13A with the oral care implement fully inserted into the case.

FIGS. 13A and 13B illustrate yet another embodiment of an oral care implement sanitization system 1000d. Features of the oral care implement sanitization system 1000d that are similar to features of the oral care implement sanitization systems 1000-1000c described above with regard to FIGS. 4-12 will be similarly numbered except that the suffix "d" will be used. It should be appreciated that for features of the oral care implement sanitization system 1000d that are numbered but not described, the description of the similar feature with regard to the oral care implement sanitization systems 1000-1000c is applicable.

In this embodiment, the oral care implement 100d comprises a body 101d comprising a handle portion 110d and a head portion 120d. A plurality of tooth cleaning elements 111d extend from the head portion 120d. Furthermore, the oral care implement 100d comprises a light source 130d that is configured to sanitize the tooth cleaning elements 111d. The light source 130d is illustrated as being located in the head portion 120d, but it may be positioned at other locations within the body 101d. The oral care implement 100d also comprises a first electrical coupling element 105d operably coupled to the light source 130d. In this embodiment, the first electrical coupling element 105d is a secondary (or receiver) coil that is configured to supply power to the light source 130d as described in more detail below.

In this embodiment, the case 200d comprises a housing 210d having a cavity 211d that is configured to hold the oral care implement 100d therein for storage and/or activation of the light source 130d. The case 200d also comprises a power source 215d and a second electrical coupling element 205d. In this embodiment, the second electrical coupling element 205d is a primary (or transmitter) coil.

FIG. 13B illustrates the system 1000d with the oral care implement 100d fully inserted into the cavity 211d of the housing 210d of the case 200d. When the oral care implement 100d is positioned within the case 200d, the first and second electrical coupling elements 105d, 205d are positioned near one another such that they are spaced apart by a distance that is less than a predetermined threshold distance. Specifically, the first and second electrical coupling elements 105d, 205d, which are primary and secondary coils, are positioned close enough to one another to ensure that the first electrical coupling element 105d (i.e., secondary coil) is located within a magnetic field created by the second electrical coupling element 205d (i.e., primary coil).

Thus, the system 1000d is capable of operation using inductive (or wireless) energy transfer rather than a direct contact-to-contact coupling of electrical components. Specifically, when the oral care implement 100d is in the case 200d, an alternating current may be sent to the second electrical coupling element 205d (i.e., the primary coil) from a transmitter circuit. In the exemplified embodiment, the transmitter circuit is included in the processor 240d, although it could be a separate component in other embodiments. The processor 240d may be coupled to the second electrical coupling element 205d. Thus, at the appropriate time the processor/transmitter circuit 240d sends an alternating current to the second electrical coupling element 205d to create a magnetic field. The first electrical coupling element 105d (i.e., secondary coil) of the oral care implement 100d is located so as to be within the magnetic field of the second electrical coupling element 205d when the oral care implement 100d is properly located within the case 200d. The magnetic field generated by the second electrical coupling element 205d results in the generation of a current within the first electrical coupling element 205d (i.e., the secondary coil). Due to the operable coupling of the first electrical coupling element 105d to the light source 130d, this current is transmitted to the light source 130d thereby activating the light source 130d to generate and transmit the UV light 222d as described herein above with regard to previous embodiments. Thus, the embodiment of FIG. 13A/13B differs from those previously described in that it uses induction to wirelessly transmit energy from the power source 215d in the case 200d to the light source 130d to activate the light source 130d. Wireless power transfer can also be used with the additional concepts disclosed with reference to FIGS. 10-12.

Figure 14A:
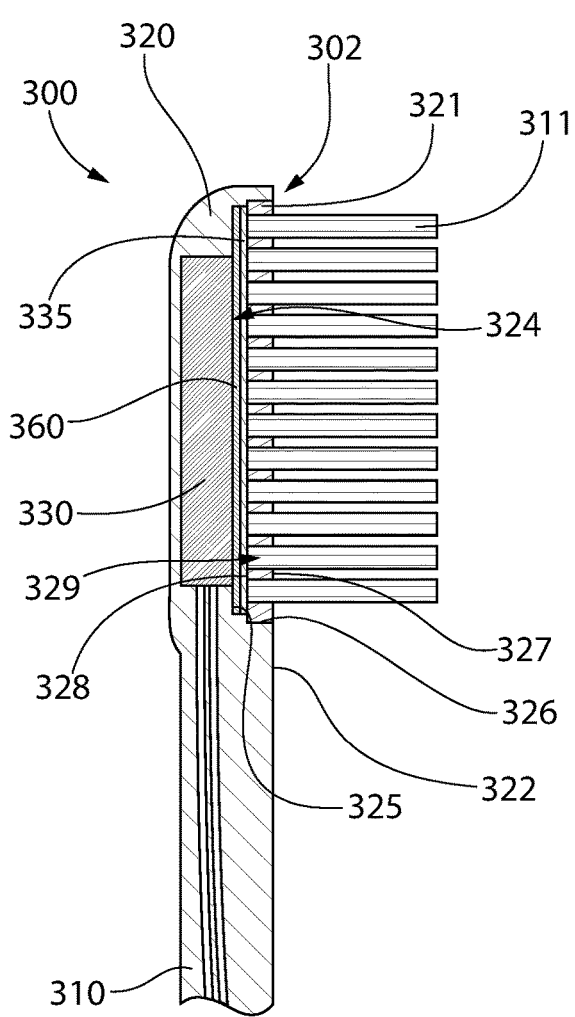
FIG. 14A is a cross-sectional view of a head portion of an oral care implement in accordance with a first alternative embodiment of the present invention.
Figure 14B:
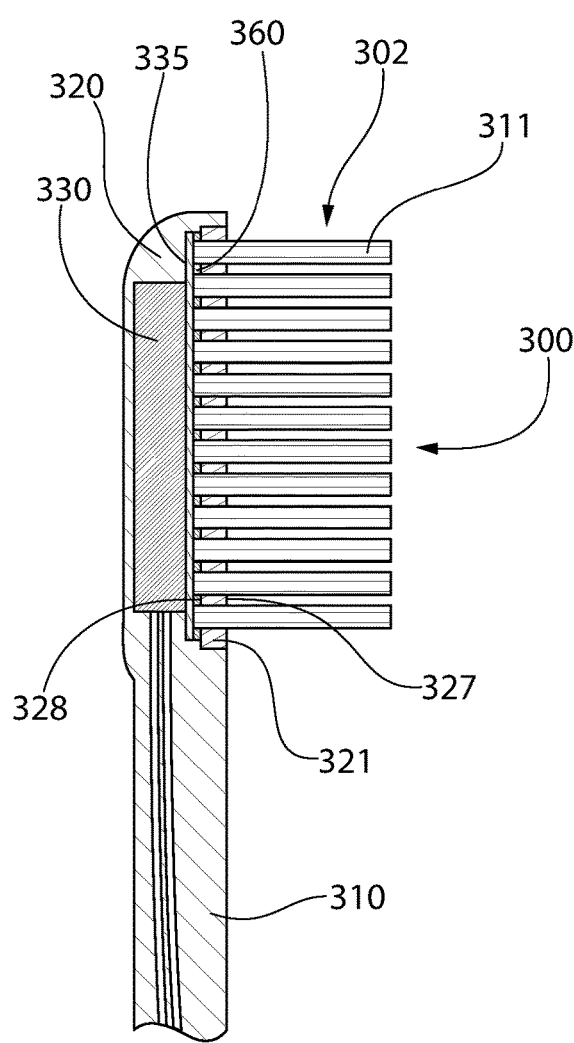
FIG. 14B is a cross-sectional view of a head portion of an oral care implement in accordance with a second alternative embodiment of the present invention.

Referring now to FIGS. 14A and 14B, a head 302 of an oral care implement 300 is illustrated in cross-section. FIGS. 14A and 14B are similar to that which is illustrated in FIG. 3B, except for the differences described herein. FIGS. 14A and 14B are substantially identical to one another except with regard to the location of an antibacterial enhancement material 360. This difference will be noted with some detail below.

The oral care implement 300 generally comprises a body 301 having a handle portion 310 and a head portion 320. The head portion 320 has a basin 324 formed therein that is defined by a floor 325 and sidewalls 326 extending from the floor 325 to a front surface 322 of the head portion 320. The head 302 of the oral care implement 300 also comprises a head plate 321 having tooth cleaning elements 311 extending therefrom. The head plate 321 has a front surface 327 and an opposite rear surface 328 and a plurality of tuft holes 329 extending therethrough. The tooth cleaning elements 311 are coupled to the head plate 321 using AFT. Specifically, the tooth cleaning elements 311 are grouped together into tufts and then each of the tufts is inserted into one of the tuft holes 329 of the head plate 321. The portions of the tufts that extend from the rear surface 328 of the head plate 321 are melted together to form a melt mat 335.

The head plate 321 with the tooth cleaning elements 311 coupled thereto is inserted into the basin 324 and coupled to the head portion 320 using techniques described in detail above (such as ultrasonic welding or the like). The head 302 also includes a light source 330 similar to that which has been described above. The main difference in this embodiment relative to those that were previously described is the inclusion of an antibacterial enhancement material 360 within the basin 324. In FIG. 14A, the antibacterial enhancement material 360 is formed as an insert that is located between the floor 325 of the basin 324 and the melt mat 335. In FIG. 14B, the antibacterial enhancement material 360 is formed as an insert that is located between the melt mat 335 and the rear surface 328 of the head plate 321. In both locations, the antibacterial enhancement material 360 is located between the light source 330 and the rear surface 328 of the head plate 321. This ensures that light emitted from the light source 330 will pass through the antibacterial enhancement material 360 before passing onto the tooth cleaning elements 311.

In the embodiment of FIG. 14B where the antibacterial enhancement material 360 is located between the melt mat 335 and the rear surface 328 of the head plate 321, the antibacterial enhancement material 360 includes holes that permit the tufts of the tooth cleaning elements 311 to pass therethrough. In FIG. 14A where the antibacterial enhancement material 360 is located between the melt mat 335 and the light source 330, the antibacterial enhancement material 360 may not include the holes because they are unnecessary due to the tooth cleaning elements 311 not needing to pass through the antibacterial enhancement material 360.

The antibacterial enhancement material 360 may be a mesh component that can be dropped into the basin 324 before the head plate 321 is inserted into the basin 324 (FIG. 14A). Alternatively, the antibacterial enhancement material 360 may be a mesh component that can be disposed adjacent the rear surface 328 of the head plate 321 before the tooth cleaning elements 311 are inserted into the tuft holes 329 of the head plate 321.

As alternatives to the location of the antibacterial enhancement material 360 shown in FIGS. 14A and 14B, the antibacterial enhancement material may also be provided as a coating on or infusion into the tooth cleaning elements 311, as a staple coating when staple technology is used to couple the tooth cleaning elements 311 to the head 302, or as a coating on or infusion into the head plate 321. In each of these alternative embodiments, the light from the light source 330 will pass through the antibacterial enhancement material before (or during) contact with the tooth cleaning elements 311 to enhance the sanitization effects of the UV light emitted from the light source 330. As noted above, the antibacterial enhancement material may be titanium dioxide ($TiO_2$), silver (Ag), zinc oxide (ZnO), or tin dioxide ($SnO_2$), although other materials known for their antibacterial enhancement capabilities may also be used in other embodiments.

Although the drawings provided herein illustrate a manual toothbrush, it should be appreciated that the same techniques can be used for a powered toothbrush. Specifically, such a powered toothbrush may include a handle and a head that are detachably coupled together. The head may be considered a refill head. The handle includes a gripping portion and a stem. The head includes a sleeve that couples to the stem of the handle. The handle and the head may be stored in a detached state such that the handle and the head are stored in separate cavities/recesses within a case. Alternatively, the handle and the head may be stored in an attached state. Regardless, the head and the case may include the electronic components described herein such that when the head is placed within the case, a light source in the head is activated to emit UV light and sanitize the tooth cleaning elements. In some embodiments the case may only store the head and not also the handle with the same results of activation of a UV light source being achieved.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement sanitization system comprising:
   an oral care implement comprising:
   a handle and a head having a plurality of tooth cleaning elements extending therefrom; and
   a light source configured to sanitize the plurality of tooth cleaning elements, wherein the oral care implement is devoid of any power source;
   a case for storing the oral care implement and powering the light source to sanitize the plurality of tooth cleaning elements, the case comprising:
   a housing comprising a cavity for holding at least a portion of the oral care implement;
   one or more batteries located within the housing; and
   wherein when the oral care implement is positioned within the cavity of the housing of the case, the one or more batteries are operably coupled to the light source to power the light source.

2. The oral care implement sanitization system according to claim 1 wherein the oral care implement comprises a first electrical coupling element operably coupled to the light source and wherein the case comprises a second electrical coupling element operably coupled to the one or more batteries, and wherein when the oral care implement is positioned within the cavity of the housing of the case, the first and second electrical coupling elements are operably coupled together so that power from the one or more batteries can be supplied to the light source.

3. The oral care implement sanitization system according to claim 2 wherein the first electrical coupling element is located on the handle of the oral care implement, and wherein the at least a portion of the oral care implement comprises the handle of the oral care implement such that the handle of the oral care implement nests within the cavity of the housing during activation of the light source to sanitize the plurality of tooth cleaning elements.

4. An oral care implement sanitization system comprising:
an oral care implement comprising:
a body having a handle portion and a head portion, a plurality of tooth cleaning elements extending from the head portion;
a light source located in the body and configured to sanitize the plurality of tooth cleaning elements; and
a first electrical coupling element operably coupled to the light source; and
wherein the oral care implement is devoid of any power source;
a case for storing the oral care implement and powering the light source to sanitize the plurality of tooth cleaning elements, the case comprising:
a housing comprising a cavity for holding at least a portion of the oral care implement;
one or more batteries located within the housing; and
a second electrical coupling element operably coupled to the one or more batteries;
wherein when the oral care implement is positioned within the cavity of the housing of the case, the first electrical coupling element of the oral care implement is operably coupled to the second electrical coupling element of the case such that power can be supplied from the one or more batteries of the case to the light source of the oral care implement.

5. The oral care implement sanitization system according to claim 4 wherein the light source is located in the head portion of the oral care implement.

6. The oral care implement sanitization system according to claim 4 wherein the oral care implement further comprises a head plate coupled to the head portion of the body, the head portion of the body comprising a basin within which the head plate is disposed, and wherein the plurality of tooth cleaning elements are coupled to and extend from a front surface of the head plate, wherein the head plate comprises the front surface, an opposite rear surface, and holes extending therethrough, wherein the plurality of tooth cleaning elements extend through the holes so that first portions of the plurality of tooth cleaning elements extend from the front surface of the head plate and second portions of the plurality of tooth cleaning elements extend from the rear surface of the head plate, and wherein the second portions of the plurality of tooth cleaning elements are melted together to form a melt mat that is positioned between the opposite rear surface of the head plate and a floor of the basin of the head portion of the body.

7. The oral care implement sanitization system according to claim 6 further comprising an antibacterial enhancement material located in the basin between the light source and the opposite rear surface of the head plate, wherein the antibacterial enhancement material is selected from the group consisting of titanium dioxide, silver, zinc oxide, and tin dioxide.

8. The oral care implement sanitization system according to claim 7 wherein the antibacterial enhancement material is located between the melt mat and the rear surface of the head plate.

9. The oral care implement sanitization system according to claim 4 wherein the case further comprises a cover that closes an open top end of the cavity, and wherein the housing and the cover collectively circumferentially surround an entirety of the oral care implement such that no portion of the oral care implement is exposed.

10. The oral care implement sanitization system according to claim 4 wherein the first electrical coupling element comprises a first pair of electrical contacts that are located on a portion of the handle portion of the body and wherein the second electrical coupling element comprises a second pair of electrical contacts located within a first portion of the cavity that receives the portion of the handle portion of the body so that the first and second pairs of electrical contacts contact one another when the oral care implement is disposed within the cavity of the housing of the case.

11. The oral care implement sanitization system according to claim 4 further comprising a processor operably coupled to the one or more batteries, and wherein upon the first and second electrical coupling elements becoming operably coupled, the processor is configured to automatically activate the light source for a predetermined period of time and to then automatically deactivate the light source after expiration of the predetermined period of time.

12. The oral care implement sanitization system according to claim 4 wherein the case further comprises a cover that is alterable between an open state and a closed state, wherein when the first and second electrical coupling elements are operably coupled together and the cover is in the open state, the light source is maintained in a deactivated state, and wherein when the first and second electrical coupling elements are operably coupled together and the cover is in the closed state, the light source is activated.

13. The oral care implement sanitization system according to claim 4 wherein when the first and second electrical coupling elements are operably coupled together, the light source is automatically activated to transmit UV light to the plurality of tooth cleaning elements for a predetermined period of time.

14. The oral care implement sanitization system according to claim 4 wherein the housing of the case comprises a compartment within which the one or more batteries are located, and wherein the compartment is closed by a door that is configured to be opened to provide a user with access to the one or more batteries located within the compartment.

15. An oral care implement sanitization system comprising:
an oral care implement comprising:
a handle and a head having a plurality of tooth cleaning elements extending therefrom;
a light source configured to sanitize the plurality of tooth cleaning elements; and
a first electrical contact element and a second electrical contact element located on the handle and operably coupled to the light source;
a case for storing the oral care implement and powering the light source to sanitize the plurality of tooth cleaning elements, the case comprising:

a housing comprising a cavity for holding at least the handle of the oral care implement;

one or more batteries located within the housing;

a first electrical contact element and a second electrical contact element located along the cavity of the housing, the first electrical contact element of the case being operably coupled to the one or more batteries;

a third electrical contact element and a fourth electrical contact element located along a distal end of the housing, the third electrical contact element operably coupled to the one or more batteries and the fourth electrical contact element operably coupled to the second electrical contact element of the case; and a cover detachably coupled to the housing, the cover comprising a metal ring;

wherein when the handle of the oral care implement is positioned within the cavity of the case, the first and second electrical contact elements of the oral care implement are in engagement with the first and second electrical contact elements of the case; and wherein when the cover is coupled to the housing, the metal ring of the cover is in engagement with the third and fourth electrical contact elements of the housing.

* * * * *